US012714790B2

(12) United States Patent
Arcolin et al.

(10) Patent No.: US 12,714,790 B2
(45) Date of Patent: Aug. 25, 2026

(54) DEVICE FOR SUBCUTANEOUS DELIVERY OF A MEDICAMENT

(71) Applicant: Nuova OMPI S.r.l. Unipersonale, Padua (IT)

(72) Inventors: Massimo Arcolin, Martinengo (IT); Nicola Bonserio, Giovinazzo (IT); Mattia Cattaneo, Limbiate (IT); Paolo Degan, Ranica (IT); Ilaria Nicoli, Parma (IT); Gaia Giulia Pieri, Milan (IT); Christian Riva, Cinisello Balsamo (IT)

(73) Assignee: Nuova Ompi S.r.l. Unipersonale, Piombino Dese (IT)

( * ) Notice: Subject to any disclaimer, the term of this patent is extended or adjusted under 35 U.S.C. 154(b) by 425 days.

(21) Appl. No.: 18/526,710

(22) Filed: Dec. 1, 2023

(65) Prior Publication Data

US 2024/0181160 A1 Jun. 6, 2024

(30) Foreign Application Priority Data

Dec. 1, 2022 (IT) ........................ 102022000024783
Dec. 1, 2022 (IT) ........................ 102022000024786

(Continued)

(51) Int. Cl.
*A61M 5/20* (2006.01)

(52) U.S. Cl.
CPC ..... *A61M 5/2033* (2013.01); *A61M 2005/206* (2013.01); *A61M 2005/2073* (2013.01)

(58) Field of Classification Search
CPC .............. A61M 5/14248; A61M 5/326; A61M 2005/14256; A61M 2005/14252
See application file for complete search history.

(56) References Cited

U.S. PATENT DOCUMENTS 5,931,814 A 8/1999 Alex et al.
7,147,624 B2 12/2006 Hirsiger et al.
(Continued)

FOREIGN PATENT DOCUMENTS

CH 712891 3/2018
EP 1764125 3/2011
(Continued)

OTHER PUBLICATIONS

Search Report in Italian Appln. No. 202200024783, mailed May 25, 2023, 9 pages.

(Continued)

*Primary Examiner* — William R Carpenter
(74) *Attorney, Agent, or Firm* — Fish & Richardson P.C.

(57) ABSTRACT

A device for subcutaneous delivery of a medicament includes an injection needle and an injection needle movement mechanism to move the injection needle between a rest position and an injection position. The injection needle movement mechanism includes a pushing member movable from a first service position to a second service position, and a support member movable between a first operating position and a second operating position. The support member also includes a coupling portion coupled to a flexible tube connected to the injection needle. The injection needle movement mechanism includes a first compression spring configured to move the pushing member from the first service position to the second service position, and a second compression spring configured to move the support member from the second operating position to the first operating position.

19 Claims, 24 Drawing Sheets

(30) Foreign Application Priority Data

| | | |
|---|---|---|
| Dec. 1, 2022 | (IT) | 102022000024801 |
| Dec. 1, 2022 | (IT) | 102022000024807 |
| Dec. 1, 2022 | (IT) | 102022000024813 |

(56) References Cited

U.S. PATENT DOCUMENTS

| | | | | |
|---|---|---|---|---|
| 7,785,288 | B2 | 8/2010 | Mernoe et al. | |
| 8,157,769 | B2 | 4/2012 | Cabiri | |
| 9,492,610 | B2 | 11/2016 | Cabiri | |
| 9,764,092 | B2 | 9/2017 | Cabiri | |
| 10,092,691 | B2 | 10/2018 | Searle et al. | |
| 10,251,995 | B2 | 4/2019 | Giambattista et al. | |
| 10,307,529 | B2 | 6/2019 | Gregory | |
| 10,518,029 | B2 | 12/2019 | Giambattista et al. | |
| 10,737,016 | B2 | 8/2020 | Smith et al. | |
| 10,881,811 | B2 | 1/2021 | Koch et al. | |
| 11,103,680 | B2 | 8/2021 | Cole | |
| 11,400,215 | B2 | 8/2022 | Cowe et al. | |
| 11,439,748 | B2 | 9/2022 | Giambattista et al. | |
| 2008/0188810 | A1 | 8/2008 | Larsen et al. | |
| 2008/0269687 | A1* | 10/2008 | Chong | A61M 5/1413 604/180 |
| 2011/0166512 | A1 | 7/2011 | Both et al. | |
| 2013/0060233 | A1 | 3/2013 | O'Connor et al. | |
| 2014/0171881 | A1 | 6/2014 | Cabiri | |
| 2016/0213837 | A1* | 7/2016 | Schabbach | A61M 5/14244 |
| 2017/0043133 | A1* | 2/2017 | Amano | A61M 25/0612 |
| 2017/0182242 | A1 | 6/2017 | Galitz et al. | |
| 2017/0224915 | A1* | 8/2017 | Destefano | A61M 5/14248 |
| 2017/0296741 | A1 | 10/2017 | Gregory | |
| 2018/0021508 | A1 | 1/2018 | DeStefano et al. | |
| 2018/0236163 | A1 | 8/2018 | Stefanov et al. | |
| 2018/0236173 | A1 | 8/2018 | McCaffrey et al. | |
| 2019/0060571 | A1 | 2/2019 | Cabiri | |
| 2019/0160225 | A1* | 5/2019 | Verlaak | A61M 5/14248 |
| 2020/0016329 | A1* | 1/2020 | Schabbach | A61M 5/148 |
| 2020/0222624 | A1 | 7/2020 | DeStefano et al. | |
| 2021/0030963 | A1 | 2/2021 | Dasbach et al. | |
| 2021/0046252 | A1 | 2/2021 | Koch et al. | |
| 2021/0138151 | A1* | 5/2021 | Scheurer | A61M 5/158 |
| 2021/0162126 | A1 | 6/2021 | Barkhuff et al. | |
| 2021/0196892 | A1 | 7/2021 | Dasbach et al. | |
| 2022/0031940 | A1 | 2/2022 | Hulliger et al. | |
| 2022/0096740 | A1 | 3/2022 | Seki et al. | |
| 2022/0143306 | A1* | 5/2022 | Yavorsky | A61M 5/158 |
| 2022/0143307 | A1 | 5/2022 | Smith | |
| 2022/0211952 | A1* | 7/2022 | Beguin | A61M 5/14248 |
| 2022/0387706 | A1 | 12/2022 | De Donatis et al. | |
| 2024/0123142 | A1 | 4/2024 | Cattaneo et al. | |
| 2024/0181155 | A1 | 6/2024 | Brasset et al. | |
| 2024/0207511 | A1 | 6/2024 | Bellusci et al. | |

FOREIGN PATENT DOCUMENTS

| | | |
|---|---|---|
| EP | 1744685 | 10/2012 |
| EP | 2646077 | 6/2015 |
| EP | 3260149 | 12/2017 |
| EP | 2836253 | 7/2019 |
| EP | 3439715 | 3/2021 |
| EP | 3862037 | 8/2021 |
| EP | 4059537 | 9/2022 |
| WO | WO 2002002165 | 1/2002 |
| WO | WO 2003099358 | 12/2003 |
| WO | WO 2006024650 | 3/2006 |
| WO | WO 2006077262 | 7/2006 |
| WO | WO 2015071289 | 5/2015 |
| WO | WO 2015187797 | 12/2015 |
| WO | WO 2018166699 | 9/2018 |
| WO | WO 2020128821 | 6/2020 |
| WO | WO 2021122671 | 6/2021 |
| WO | WO 2021166699 | 8/2021 |
| WO | WO 2021252971 | 12/2021 |

OTHER PUBLICATIONS

Search Report in Italian Appln. No. 202200024786, mailed May 26, 2023, 7 pages.

Search Report in Italian Appln. No. 202200024792, mailed May 30, 2023, 7 pages.

Search Report in Italian Appln. No. 202200024801, mailed May 24, 2023, 9 pages.

Search Report in Italian Appln. No. 202200024807, mailed May 26, 2023, 8 pages.

Search Report in Italian Appln. No. 202200024813, mailed Jun. 5, 2023, 11 pages.

Search Report in Italian Appln. No. 202200026286, mailed Jun. 13, 2023, 7 pages.

* cited by examiner 60
54
63
62
61b
11
36a
36
36b
61c
63d
61e
61a
61
63c
62a 60
63
61e
54
61b
62
11
36
61
63d 60
P
36
11
83
83a
80
70
34
62a
N
62b
62
C
72
E
70a
630
64
63a
63
D
65

1
P
11
83
83a
62
62a
70
70a
N
C
71
E
70e
72
80
64
D
60
630
62b
63a
61b
65
15
56
A
F

DEVICE FOR SUBCUTANEOUS DELIVERY OF A MEDICAMENT

CROSS REFERENCE TO RELATED APPLICATIONS

The present application claims priority to Italian Patent Application No. 102022000024786, filed on Dec. 1, 2022, Italian Patent Application No. 102022000024801, filed Dec. 1, 2022, Italian Patent Application No. 102022000024783, filed Dec. 1, 2022, Italian Patent Application No. 102022000024807, filed Dec. 1, 2022, and Italian Patent Application No. 102022000024813, filed Dec. 1, 2022, the disclosures of which are incorporated herein by reference in their entirety.

TECHNICAL FIELD

The present disclosure relates to a device for subcutaneous delivery of a medicament. In particular, the present disclosure relates to a wearable type device configured to be applied on the body of a patient in order to allow the subcutaneous delivery of a predetermined dose of medicament.

BACKGROUND

Wearable delivery devices can include medicament that is initially contained in a cartridge housed within the device and is transferred to the body of the patient via a fluidic path. The cartridge can include a cylindrical container, made of a plastic or glass material, a plunger slidable inside the container to push the medicament out of the container and a pierceable septum that guarantees the sterility of the container until the beginning of the delivery of the therapy. Typically, the fluidic path of wearable delivery devices includes a piercing needle to pierce the pierceable septum of the cartridge and a flexible tube that puts the piercing needle in fluid communication with an injection needle. The container of the cartridge is kept closed by the pierceable septum until the delivery of the medicament is required. When such a delivery is required, the piercing needle pierces the pierceable septum and opens the fluidic path, allowing the medicament to reach the patient by initially passing through the piercing needle, then through the flexible tube and finally through the injection needle, due to the thrust exerted by the plunger on the medicament inside the container.

SUMMARY OF THE DISCLOSURE

The present disclosure relates to devices for subcutaneous delivery of a medicament, including a cartridge, piercing needle, flexible tube, injection needle, and an injection needle movement mechanism. The delivery of a medicament to a patient takes place after the insertion of the injection needle into the body of the patient. Such insertion occurs following activation of the movement mechanism configured to move the injection needle between a rest position in which the injection needle is entirely arranged inside the device and an injection position in which the injection needle protrudes from the device and penetrates the skin of the patient. The movement of the injection needle from the rest position to the injection position and/or vice versa can be obtained due to the pushing action exerted by respective springs on the member that supports the injection needle.

US 2021/0162126A1 describes an auto-injector comprising a housing and a needle that can take two positions, one in which it is retracted into the housing and one in which it protrudes from the housing to penetrate the skin of the patient. The movement between the two positions can be activated electronically.

EP 1764125B1 and WO 2002/02165A2 disclose embodiments of manually operated mechanisms for moving the injection needle. In particular, in the embodiment of FIGS. 19 and 20 of WO 2002/02165A2 two coaxial compression springs 232 and 265 are provided, which are arranged one externally to the other and both around the member 270 which supports the injection needle. This arrangement implies the impossibility of laterally accessing the member 270 to connect to said member 270 the flexible tube intended to connect the piercing needle for piercing the septum of the cartridge to the injection needle. This flexible tube must therefore necessarily be connected to an upper surface of the member 270 and extend vertically or almost vertically above said upper surface and then flexing so as to reach the piercing needle. However, this flexing of the flexible tube during use generates a risk of reduction of the section of the flexible tube and of not being able to guarantee a regular flow of the medicament towards the injection needle. Certain devices have a sufficient height to allow a suitable arrangement of the flexible tube. However, these devices can be cumbersome and uncomfortable given that they are typically expected to be used for a long time by the patient.

A device of the present disclosure can be more compact than those described earlier.

In some instances, an injection needle movement mechanism of the present disclosure uses compression springs to allow an optimal control of the driving force of the needle to extract the injection needle from the device and to retract the injection needle into the device. This control is advantageous in limiting as much as possible the pain felt by the patient during the penetration of the injection needle into his/her body and the extraction of the injection needle from his/her body.

A flexible tube can be connected to a side surface of the member which supports the injection needle to reduce the height of the device as much as possible and thus make it sufficiently compact and comfortable for a prolonged use by the patient, and the extraction of the injection needle from the device and the retraction of the injection needle into the device is achieved by providing compression springs, so as to be able to optimally control the driving force of the injection needle during the insertion of the injection needle into the body of the patient and the extraction of the injection needle from the body of the patient.

The present disclosure therefore relates, in a first aspect thereof, to a device for subcutaneous delivery of a medicament, comprising:

- an injection needle configured to receive the medicament from a cartridge through a flexible tube and to inject the medicament to a patient;
- an injection needle movement mechanism configured to move the injection needle between a rest position in which the injection needle is entirely arranged within the device and an injection position in which the injection needle protrudes at least partially from the device;

wherein the injection needle movement mechanism comprises:

- a pushing member movable from a first service position in which the injection needle is in the rest position to a second service position in which the injection needle is in the injection position;
- a first compression spring associated with the pushing member and configured to exert on the pushing member a force that is suitable for moving the pushing member from the first service position to the second service position, the first compression spring extending along a first axis;
- a support member on which the injection needle is mounted, the support member being movable between a first operating position in which the injection needle is in the rest position and a second operating position in which the injection needle is in the injection position, the support member comprising, on an outer side surface thereof, a coupling portion coupled to the flexible tube;
- a second compression spring associated with an inner surface of the support member and configured to exert on the support member a force that is suitable for moving the support member from the second operating position to the first operating position, the second compression spring extending along a second axis that is distinct from the first axis;
- wherein the injection needle movement mechanism has a first operating configuration in which the pushing member is coupled to the support member and the force exerted by the first compression spring on the pushing member moves the pushing member from the first service position to the second service position and the support member from the first operating position to the second operating position loading the second compression spring, and a second operating configuration in which the pushing member is decoupled from the support member and the force exerted by the second compression spring on the support member moves the support member from the second operating position to the first operating position.

These, and other aspects, can include one or more of the following features. When the injection needle movement mechanism is in the second operating configuration, the pushing member is in the second service position. The first compression spring can have a first elastic constant greater than a second elastic constant of the second compression spring. The pushing member can be movable around the first axis from a first angular position in which the injection needle movement mechanism is in the first operating configuration to a second angular position in which the injection needle movement mechanism is in the second operating configuration. The support member can include an abutment element and the pushing member can include a pushing element which, when the injection needle movement mechanism is in the first operating configuration, exerts a pushing action against the abutment element. The abutment element can protrude from the outer side surface of the support member towards the pushing member and the pushing element can protrude from an outer side surface of the pushing member towards the support member. The injection needle movement mechanism can include a command member configured to move the pushing member from the first angular position to the second angular position. The command member can be movable around the first axis from a stop angular position in which the pushing member is in the first angular position and the command member can be coupled to the pushing member and can keep the pushing member in the first service position, to a first release angular position in which the pushing member is in the first angular position and the command member is decoupled from the pushing member allowing the pushing member to reach the second service position. The pushing member can include a protruding element, and the command member can include an abutment surface configured to abut against the protruding element when the command member is in the stop angular position, and a seat configured to house the protruding element when the command member is in the first release angular position. The command member can be movable around the first axis from the first release angular position to a second release angular position in which the pushing member is in the second angular position. When the command member is in the second release angular position, the protruding element is housed in the seat. The device can include a motion transmission member configured to activate the shift of the injection needle movement mechanism from the first operating configuration to the second operating configuration. The command member can include a coupling portion coupled to the motion transmission member. The motion transmission member can include a rack and an endless screw engaged to the rack at the coupling portion, and the command member can include a toothing engaged to the endless screw.

In the present description and in the subsequent claims, the term "compression spring" is used to indicate a spring, typically comprising a plurality of coils, which is used to offer resistance to a force that tends to compress it. Therefore, when this spring is at rest it is in an expanded configuration while when the spring is loaded by the abovementioned force it is in a contracted configuration.

The device of the disclosure thus comprises two compression springs that are non-coaxial to each other and active on distinct members. The first compression spring acts on the pushing member to command the movement of the injection needle from inside to outside of the device prior to initiating the delivery of the therapy while the second compression spring acts on the support member of the injection needle to return the injection needle inside the device at the end of the delivery of the therapy. The second compression spring, in particular, acts on an inner surface of the support member which supports the injection needle. In this way the outer side surface of the support member remains always accessible and it is therefore possible to couple the flexible tube to it. It is thus possible to reduce the height dimension of the device, to the benefit of use comfort for the patient.

The present disclosure also relates to another device having all the features of the device described above and in which:

- the injection needle is arranged outside its support member;
- the flexible tube is connected directly to the support needle;
- the first compression spring and the second compression spring are coaxial to each other.

It is desirable that the drug delivery devices are safe, accurate, and easy to use. This combination of requirements makes these devices very expensive to produce and consequently very expensive for the patients.

There is therefore the need to provide a fluidic path opening system that is simple (to reduce the production costs of the device), compact (to minimise the volume occupied by the device and make the device as comfortable as possible when applied on the body of the patient) and solid (to ensure the correct operation of the device). It is also necessary that, once the fluidic path opening system is activated, the piercing needle penetrates the pierceable septum in an automatic and controlled manner. In fact, it is appropriate to calibrate the penetration force so as to allow the piercing needle to completely pass through the pierceable septum (so as to actually open the fluidic path), while avoiding an excessive penetration of the piercing needle into the container of the cartridge (so that the piercing needle is not closed by the plunger of the cartridge during the delivery of the medicament).

Examples of devices comprising fluidic path opening systems suitable for allowing an automatic and controlled movement of the piercing needle are described in U.S. Ser. No. 10/569,014B2 and EP 3862037A1.

In particular, the fluidic path opening system of the device of EP 3862037A1 comprises a piercing needle movement mechanism 70 having two configurations, a first rest configuration in which the movement mechanism is not driven and the piercing needle 70 is in a distal position with respect to the septum of the cartridge (position of FIG. 9) and a second operating configuration in which the movement mechanism is driven and the piercing needle 70 has pierced the septum of the cartridge (position of FIG. 11). The piercing needle 70 is mounted on a support member 80 which, thanks to the pushing action exerted by a compression spring 90, can translate from the position of FIG. 9 to that of FIG. 11. The piercing needle movement mechanism 70 is activated by a linear translational movement of a control element 40. With reference to FIG. 9, the compression spring 90 is initially kept compressed between the control element 40 and the support member 80 due to the mutual abutment of the surfaces 47 and 81 of the control element 40 and of the support member 80, respectively. As shown in FIG. 11, due to the translation of the control element 40, the abutment between the surfaces 47 and 81 is lost and the support member 80 can reach the position of FIG. 11 due to the pushing action exerted by the compression spring 90. In some instances, to allow linear translational movement of the control element, an additional space is provided with respect to the space occupied by the control element before it is moved, to the detriment of the compactness of the device and of the use comfort for the device. Furthermore, the control element can be subjected to pressure from opposite sides, with a consequent need to exert a high driving force to move it from this position in order to reach the operating configuration.

Another technical problem solved by the present disclosure is to realize a device for subcutaneous delivery of a medicament comprising a fluidic path opening system that does not have the drawbacks discussed above.

The present disclosure therefore relates, in a further aspect thereof, to a device for subcutaneous delivery of a medicament, comprising:

- a cartridge comprising a container containing the medicament and a pierceable septum coupled to an end of the container;
- a piercing needle configured to pierce the pierceable septum;
- an injection needle configured to inject the medicament to a patient, the injection needle defining with the piercing needle a fluidic path configured to be travelled by the medicament during the subcutaneous delivery of the medicament;
- a fluidic path opening system configured to put the injection needle in fluid communication with the container through the piercing needle;

wherein the fluidic path opening system comprises:

- a support member on which the piercing needle is mounted, the support member being movable between a first operating position in which the piercing needle is spaced apart from the pierceable septum and the fluidic path is closed, and a second operating position in which the piercing needle has pierced the pierceable septum, and the fluidic path is open;
- an elastic element configured to exert on the support member a pushing action that is suitable for moving the support member from the first operating position to the second operating position;
- a driving member rotatable around a rotation axis and movable from a first angular position in which the driving member keeps the support member in the first operating position counteracting the pushing action of the elastic element to a second angular position in which the support member is free to move from the first operating position to the second operating position due to the pushing action of the elastic element.

These, and other aspects, can include one or more of the following features. The device can include a motion transmission member configured to activate the movement of the driving member, where the driving member can include a first coupling portion configured to couple to the motion transmission member and a second coupling portion configured to couple to the support member. The driving member can include a base body, and the first coupling portion and second coupling portion can extend on opposite sides from the base body. The motion transmission member can include a rack, and the first coupling portion can include a toothing engaged to the rack. The second coupling portion can include a perimeter wall provided with a through opening. The support member can include an abutment element configured to be in abutment against an outer surface of the perimeter wall when the driving member is in the first angular position and at the through opening when the driving member is in the second angular position. The driving member can be movable until it reaches a third angular position in which the driving member prevents the support member from moving from the second operating position to the first operating position. The perimeter wall can delimit in the driving member an area configured to receive the abutment element when the driving member is in the second angular position, and when the driving member is in the third angular position, the abutment element can be at an inner surface of the perimeter wall. The support member can include a body and the abutment element can protrude from the body. The elastic element can be a torsion spring including a plurality of coils arranged around an axis parallel or orthogonal to the rotation axis.

The fluidic path opening system of the device of the present disclosure therefore comprises a driving member which, being rotatable, does not need additional space when it is moved to drive the movement of the piercing needle and the consequent piercing of the pierceable septum, to the benefit of the compactness and use comfort of the device. Moreover, the rotation of the driving member can be obtained without the need to apply high driving forces.

The needle movement mechanism can extract the injection needle from the skin of the patient at the end of the delivery of the therapy bringing it back inside the device.

The use of shielding elements configured to protect the patient from accidental contacts with the injection needle at the end of the administration of the therapy is known.

WO 2002/02165A2 describes different embodiments of shielding elements which, thanks to the action of a spring, are activated following removal of the device from the skin of the patient. In particular, the embodiment of FIGS. 17-20 of WO 2002/02165A2 provides for an automatic movement of extraction of a shielding element 231 which is initially locked inside the device in a retracted position (FIGS. 17 and 18) and which only when the device is moved away from the skin of the patient exits the device due to the thrust exerted by a spring 232, thus covering the injection needle N (FIG. 20). The unlocking of the shielding element 231 is functionally connected to the movement of the injection needle N from inside to outside the device. This movement in fact causes the breakage of yielding elements that constrain the shielding element 231 in the retracted position. It is provided for the shielding element 231 to remain locked in position once removed from the device.

Also in the device described in U.S. Ser. No. 10/881,811B2 the shielding element is initially locked inside the device and is then unlocked to exit the device and cover the injection needle when the device is moved away from the skin of the patient. Also in this device, the extraction of the shielding element takes place due to the pushing action exerted by a spring and, once extracted from the device, the shielding element remains locked in place. In this case, however, the extraction of the shielding element is functionally independent on the movement of the injection needle and requires a prior rotation of the shielding element. This rotation is commanded only at the end of the delivery of the medicament.

In devices where the extraction of the shielding element is functionally independent on the movement of the injection needle, the latter could accidentally exit the device before applying the device on the skin of the patient, for example because of a malfunction of the injection needle movement mechanism or because of a voluntary or accidental activation of the device by the user. In some instances, the device can be accidentally or voluntarily removed from the skin of the patient before the end of the delivery of the therapy. In both cases, the injection needle may be outside the device while the shielding element is still locked inside the device, with a consequent risk for the patient to prick him/herself.

Another technical problem solved by the present disclosure is to realize a device in which the extraction of the shielding element is functionally independent on the movement of the injection needle and in which any possibility of voluntary or accidental contact of the patient with the tip of the injection needle is avoided both before applying the device on the skin of the patient and after having applied the device on the skin of the patient.

The present disclosure therefore relates, in a further aspect thereof, to a device for subcutaneous delivery of a medicament, comprising:

- a cartridge comprising a container containing the medicament;
- an injection needle configured to inject the medicament to a patient when the device is applied on the skin of the patient, the injection needle being movable between a rest position in which the injection needle is entirely arranged within the device and an injection position in which the injection needle protrudes at least partially from the device;
- a shielding element movable between a first operating position in which the shielding element protrudes from the device and covers the tip of the injection needle if the injection needle is in the injection position, and a second operating position in which the shielding element does not protrude from the device;
- an elastic element associated with the shielding element and configured to exert on the shielding element a pushing action which is suitable for keeping the shielding element in the first operating position both before applying the device on the skin of the patient and when the device is removed from the skin of the patient and to allow the shielding element to reach the second operating position when the device is applied on the skin of the patient;
- a stop element configured to stop the movement of the shielding element;
- wherein the shielding element comprises a locking element configured to cooperate with the stop element and to lock the shielding element in the first operating position when the device is removed from the skin of the patient.

These, and other aspects, can include one or more of the following features. The device can have a reversible initial configuration in which the stop element is in a distal position with respect to the locking element and the locking element can be movable integrally with the shielding element from the first operating position to the second operating position and vice versa, and an irreversible final configuration in which the stop element and the locking element are in mutual contact and the shielding element is locked in the first operating position. When the device is in the reversible initial configuration, the injection needle can be in the rest position, and when the device is in the irreversible final configuration, the injection needle can be in the rest position or in the injection position. The stop element can be movable from an initial position in which the stop element and the locking element are not superimposed on each other to a final position in which the stop element and the locking element are superimposed on each other. The stop element can be movable from the initial position to the final position along a first direction and the locking element can be movable integrally with the shielding element between the first operating position and the second operating position along a second direction orthogonal to the first direction. When the device is in the reversible initial configuration, the stop element can be movable along the first direction, and the device can switch from the reversible initial configuration to the irreversible final configuration when the stop element is in the final position and the locking element moves along the second direction from the second operating position to the first operating position passing beyond the stop element. One of the locking element or the stop element can be made of a rigid material and the other one of the locking element or the stop element is made of a deformable material, and the movement of the locking element along the second direction can cause an interference between the locking element and the stop element, and a deformation of the element made of a deformable material that is suitable to allow the passage of the element made of a rigid material. The locking element can be made of a rigid material and the stop element can be made of a deformable material and can include a first surface facing the locking element when the stop element is in the final position and the locking element is in the second operating position, and a second surface facing on the opposite side of the first surface and toward the locking element when the stop element is in the final position and the locking element is in the first operating position, where the first surface allows the stop element to deform due to the interference with the locking element and the locking element can move along the second direction from the second operating position to the first operating position and where the second surface can define an undercut that prevents the locking element from moving from the first operating position when the device is in the irreversible final configuration. The shielding element can include a base provided with a through hole or with a pierceable septum to allow the passage of the injection needle during the movement of the injection needle between the rest position and the injection position when the shielding element is in the second operating position, where the base can include a raised edge that defines in the shielding element a recess configured to house the tip of the injection needle both when the shielding element is in the second operating position and the injection needle is in the rest position and when the shielding element is in the first operating position and the injection needle is in the injection position. The device can include a fluidic path opening system that can be activated to put the injection needle in fluid communication with the container and where the locking element can be configured to lock the shielding element in the first operating position upon activation of the fluidic path opening system. The fluidic path opening system can include a piercing needle to pierce a pierceable septum coupled to an end of the container, a driving member configured to drive the movement of the piercing needle, and a motion transmission member configured to drive the driving member, where the stop element is associated with the motion transmission member. The device can include a position sensor configured to detect a contact of the device with the skin of the patient. The position sensor can include a magnet integrally associated with the shielding element and a Hall effect sensor arranged in the device close to the magnet. The magnet can be entirely housed in a seat formed in the shielding element. The locking element can be associated with the magnet.

In the device of the disclosure, it is provided that the shielding element is outside the device before applying the device on the skin of the patient and covers the tip of the injection needle in case the latter for some reason is outside the device or exits the device, so as to prevent the patient from coming into contact with the tip of the injection needle. If, for example, because of an accidental or voluntary removal of the device from the skin of the patient before the end of the delivery of the therapy, the injection needle remains in the extracted position, the shielding element immediately exits the device and remains locked in the extracted position, also in this case preventing the patient from coming into contact with the tip of the injection needle.

In instances where a continuous medicament release is required, the devices for subcutaneous delivery can be worn by the patient for long periods. These devices can be impermeable to water so as not to hinder the patient's daily life in activities such as having a shower, a bath, sport activities, swimming, etc. In fact, if water, or even sweat, enters inside the device, the electronic and mechanical components inside the device may suffer malfunctions or failures.

In some instances, critical points where water and/or sweat can enter inside the device can be considered, and the most critical point in terms of impermeability can be the one in which the through opening through which the injection needle exits from the device for the delivery of the therapy is provided.

WO 2021/252971A2 describes the use of a watertight barrier positioned above the abovementioned through opening.

US 2020/0222624A1 and US 2013/0060233A1 describe the use of a membrane extending inside the device around the injection needle when the needle is entirely arranged inside the device. The membrane maintains a sterile environment around the injection needle. When the injection needle comes out of the device the membrane is folded like bellows inside the device.

Many devices are provided with shielding elements arranged around the through opening through which the injection needle exits for the delivery of the therapy. These shielding elements are movable between a retracted position in which they are arranged inside the device and an extended position in which they are extracted from the device to be arranged around the injection needle when the device is removed from the skin of the patient, so as to protect the patient from accidental contacts with the injection needle at the end of the delivery of the therapy. Examples of devices of the type described above are disclosed in WO 2002/02165A2 and U.S. Ser. No. 10/881,811B2. In the devices provided with shielding elements, it is desirable to provide for measures suitable for preventing the entry into the device of water, sweat, and more generally of powders and liquids.

Another technical problem solved by the present disclosure is therefore to provide a solution suitable for preventing the entry of water, sweat and more generally of powders and liquids into devices provided with shielding elements that protrude from the device when the device is not applied on the skin of the patient and that are housed in the device when the device is applied on the skin of the patient.

In some instances, a flexible sleeve is provided around the shielding element and is capable of moving in synchrony with the shielding element, and by associating this flexible sleeve to the device water-tightly, it also becomes powder-tightly.

The present disclosure therefore relates, in a further aspect thereof, to a device for subcutaneous delivery of a medicament, comprising:

- an injection needle configured to inject the medicament to a patient when the device is applied on the skin of the patient, the injection needle being movable between a rest position in which the injection needle is entirely arranged within the device and an injection position in which the injection needle protrudes at least partially from the device through a through opening of the device;
- a shielding element arranged around the injection needle and movable between a first operating position in which the shielding element protrudes from the device and a second operating position in which the shielding element does not protrude from the device;
- a flexible sleeve associated water-tightly to the device around the through opening and integrally associated with the shielding element.

These, and other aspects, can include one or more of the following features. The shielding element can include a base provided with a through hole to allow the passage of the injection needle during the movement of the injection needle between the rest position and the injection position, and the flexible sleeve can be integrally associated with the base. The flexible sleeve can be defined by a membrane having an inner surface that is integrally associated with the outer surface of the base. The membrane can be of the bellows type and can have a substantially conical or truncated conical shape. The flexible sleeve can have a base surface integrally associated with the base of the shielding element, and the base surface can cover the through hole and can be pierceable by the injection needle when the injection needle moves from the rest position to the injection position. The through hole of the base of the shielding element can be closed by a pierceable septum configured to be pierced by the injection needle when the injection needle moves from the rest position to the injection position. The flexible sleeve can be entirely arranged within the device when the shielding element is in its second operating position. The device can include a compression ring welded to an application surface of the device at the through opening, and the flexible sleeve can include an annular end portion which is interposed between the application surface and the compression ring. The compression ring can be welded by ultrasonic welding. The flexible sleeve can be made of a silicone material for medical use.

Being integrally associated with the shielding element, the flexible sleeve moves with the shielding element between the abovementioned first operating position in which the flexible sleeve and the shielding element extend outside the device and the abovementioned second operating position in which the flexible sleeve and the shielding element are housed inside the device. Therefore, by associating the flexible sleeve with the device around the shielding element so as to be watertight, the impermeability of the device and the tightness also against the powders at the through opening through which the injection needle exits for the delivery of the therapy are ensured.

The various components of the devices described above can act in synchrony to ensure that the delivery of the medicament takes place accurately and under maximum safety conditions for the patient. However, there is the need to ensure this synchronization without making the device too complex both as regards the number of components and as regards their movement.

WO 2020/128821A1 describes a device comprising a single rotor that rotates in the two opposite rotation directions to drive the delivery of the medicament and the movement of the injection needle, respectively.

To further simplify the production and the assembly of the abovementioned devices, a reduction in production cost and, consequently, purchase cost can be attained.

In some instances, providing a single rotor, by rotating in the two opposite directions, can drive the delivery of the medicament and the movement of the injection needle, and also providing a single transmission member, by rotating in the same rotation direction, can cause the opening of the fluidic path and the extraction of the injection needle from the device for the delivery of the therapy.

The present disclosure therefore relates, in a further aspect thereof, to a device for subcutaneous delivery of a medicament, comprising:

- a cartridge comprising a container containing the medicament, a plunger slidable in the container and a pierceable septum coupled to an end of the container;
- a piercing needle configured to pierce the pierceable septum;
- an injection needle configured to inject the medicament to a patient, the injection needle defining with the piercing needle a fluidic path configured to be travelled by the medicament during subcutaneous delivery of the medicament;
- a fluidic path opening system configured to partially insert the piercing needle into the pierceable septum and thereby put the injection needle in fluid communication with the container through the piercing needle;
- an injection needle movement mechanism configured to move the injection needle between a rest position in which the injection needle is entirely arranged within the device and an injection position in which the injection needle protrudes at least partially from the device;
- a medicament delivery mechanism configured to move in a controlled manner the plunger into the container toward the pierceable septum;
- a rotor configured to control the fluidic path opening system, the injection needle movement mechanism, and the medicament delivery mechanism;
- a control unit configured to drive the rotor alternately in a first rotation direction and in a second rotation direction opposite to the first rotation direction;
- a first motion transmission member connected to the rotor and configured to drive the fluidic path opening system and the injection needle movement mechanism by rotation of the rotor in the first rotation direction;
- a second motion transmission member connected to the rotor and configured to drive the medicament delivery mechanism by rotation of the rotor in the second rotation direction.

These, and other aspects, can include one or more of the following features. The first motion transmission member can be configured to activate the fluidic path opening system when the rotor rotates in the first rotation direction for a first time interval and the injection needle movement mechanism when the rotor rotates in the first rotation direction for a second time interval. The second time interval can be subsequent to the first time interval. The device can further include a shielding element that is movable between a first operating position in which the shielding element protrudes from the device and a second operating position in which the shielding element does not protrude from the device, and a stop mechanism configured to stop the movement of the shielding element, where the stop mechanism includes a stop element and the shielding element includes a locking element configured to cooperate with the stop element and to lock the shielding element in the first operating position when the device is removed from the skin of the patient, and the first motion transmission member can be configured to drive the stop mechanism when the rotor rotates in the first rotation direction for a given time interval. The given time interval can coincide at least in part with the second time interval. The first motion transmission member can include a rack movable along a first direction and an endless screw coupled to the rack. The endless screw can be coupled to a command member which controls the injection needle movement mechanism. The rack can include a first coupling portion configured to drive a driving member of the fluidic path opening system during the movement of the rack along the first direction and a second coupling portion arranged upstream with respect to the first coupling portion along the first direction and coupled to the endless screw. The stop element can be associated with a third coupling portion of the rack arranged upstream with respect to the first coupling portion along the first direction. The third coupling portion can be interposed between the first coupling portion and the second coupling portion.

In another further aspect thereof, the present disclosure relates to a method for performing a subcutaneous delivery of a medicament through a device according to any one of the previous aspects, comprising, in sequence:

- detecting if the device is applied on the skin of the patient;
- activating the fluidic path opening system by the first motion transmission member by rotating the rotor in the first rotation direction for a first time interval;
- driving the medicament delivery mechanism by the second motion transmission member by rotating the rotor in the second rotation direction for a third time interval, causing the movement of the plunger in the container without delivery of the medicament through the injection needle;

driving the injection needle movement mechanism by the first motion transmission member by rotating the rotor in the first rotation direction for a second time interval, causing the movement of the injection needle from the rest position to the injection position;

driving the medicament delivery mechanism by the second motion transmission member by rotating the rotor in the second rotation direction for a fourth time interval, causing the movement of the plunger in the container without delivery of the medicament through the injection needle.

These, and other aspects, can include one or more of the following features. The method can further include, after driving the medicament delivery mechanism by the second motion transmission member by rotating the rotor in said second rotation direction for the fourth time interval, driving the injection needle movement mechanism by the first motion transmission member by rotating the rotor in the first rotation direction for a fifth time interval, causing the movement of the injection needle from the injection position to the rest position. The method can further include, after activating the fluidic path opening system by the first motion transmission member by rotating the rotor in the first rotation direction for the first time interval and before removing the device from the skin of the patient, driving the stop mechanism of the shielding element by the first motion transmission member by rotating the rotor in the first rotation direction for a given time interval. The given time interval can coincide at least in part with the second time interval. Activating the fluidic path opening system and driving the stop mechanism of the shielding element can include moving the rack along the first direction.

In accordance with the present disclosure, the desired reduction of the production and purchase costs of the device is achieved thanks to the reduction in the number of components necessary to perform the various phases of operation of the device. In particular, it is provided for a single rotor that when rotating in one direction drives a single motion transmission member, which in turn drives the opening of the fluidic path and the extraction of the injection needle from the device. When, on the other hand, the rotor rotates in the opposite direction, it drives another motion transmission member, which in turn drives the delivery of the medicament to the patient through the fluidic path.

Preferred features of the disclosure are described herein. Each of these features can be provided individually or in combination with the other features.

In some embodiments, when the injection needle movement mechanism is in the second operating configuration, the pushing member is in the second operating position. In particular, after the pushing member has been moved from the first service position to the second service position due to the pushing action exerted by the first compression spring and has decoupled from the support member, and while the latter returns to the first operating position due to the pushing action exerted by the second compression spring, thus returning the injection needle inside the device, the pushing member remains in the second service position, being decoupled from the support member.

In some embodiments, in the device of the disclosure the second axis is parallel to the first axis. In this way, the extension of the first compression spring causes a corresponding compression of the second compression spring, to the benefit of the functionality and effectiveness of the device.

In some embodiments, in the device of the disclosure the injection needle extends along a third axis that is distinct from the second axis. The arrangement of the springs is thus such as not to be cumbersome during the movement of the injection needle.

In some embodiments, the third axis is arranged close to the outer side surface of the support member. In this way, the coupling portion for coupling to the flexible tube can be placed close to the injection needle, thus limiting the extension of the section of fluidic path defined between the end of the flexible tube attached to the support member and the injection needle.

In some embodiments, the first compression spring has an elastic constant greater than that of the second compression spring. This expedient allows the second compression spring to be loaded when the first compression spring extends and brings the pushing member from the first service position to the second service position and, consequently, the support member which supports the injection needle from the first operating position to the second operating position.

In some embodiments, the pushing member is movable around the first axis from a first angular position in which the injection needle movement mechanism is in the first operating configuration to a second angular position in which the injection needle movement mechanism is in the second operating configuration. In this way, the shift from the first to the second operating configuration takes place without the need to provide any additional space for the pushing member with respect to the one initially occupied. This allows the plan dimensions of the device to be as small as possible.

In some embodiments, the support member comprises an abutment element.

In certain embodiments, the pushing member comprises a pushing element which, when the injection needle movement mechanism is in the first operating configuration, exerts a pushing action against the abutment element.

In some embodiments, the abutment element protrudes from the outer side surface of the support member towards the pushing member.

In certain embodiments, the pushing element protrudes from an outer side surface of the pushing member towards the support member. This expedient allows the plan dimensions of the device to be as small as possible.

In some embodiments, the injection needle movement mechanism comprises a command member configured to move the pushing member from the first angular position to the second angular position.

In some embodiments, the command member is arranged concentrically to the pushing member, so as to maintain the overall plan dimensions of the device as small as possible.

In some embodiments, the command member is movable around the first axis from a stop angular position in which the pushing member is in the first angular position and the command member is coupled to the pushing member and keeps the pushing member in the first service position, to a first release angular position in which the pushing member is in the first angular position and the command member is decoupled from the pushing member allowing the pushing member to reach the second service position. In this way, the shift of the command member from the stop angular position to the first release angular position takes place without the need to provide any additional space for the command member with respect to the one initially occupied. This allows the plan dimensions of the device to be as small as possible.

In some embodiments, the pushing member comprises a protruding element.

In certain embodiments, the command member comprises an abutment surface configured to abut against the protruding element when the command member is in the stop angular position.

In some embodiments, the command member comprises a seat configured to house the protruding element when the command member is in the first release angular position. The movement of the pushing member from the first service position to the second service position and, consequently, the movement of the support member from the first operating position to the second operating position and the extraction of the injection needle from the device takes place when the abovementioned seat is below the protruding element. Once this relative position is reached, the thrust exerted by the first compression spring on the pushing member is no longer hindered by the abutment surface of the command member and causes the pushing member to move from the first service position to the second service position.

In some embodiments, the protruding element protrudes from the outer side surface of the pushing member on the opposite side with respect to the pushing element. This expedient allows to separate spatially and functionally the portion of the pushing member configured to cooperate with the command member from the portion configured to push the support member which supports the injection needle, to the benefit of the functionality and structural simplicity of the injection needle movement mechanism.

In some embodiments, the command member comprises a through opening.

In certain embodiments, the pushing element passes through the through opening both when the pushing member is in the first service position and when the pushing member is in the second service position. In this way, the pushing element can act on the abutment element of the support member when the injection needle movement mechanism is in the first operating configuration.

In some embodiments, the command member is movable around the first axis from the first release angular position to a second release angular position in which the pushing member is in the second angular position. In this way, the shift of the command member from the first release angular position to the second release angular position takes place without the need to provide any additional space for the command member with respect to the one initially occupied. This allows the plan dimensions of the device to be as small as possible.

In some embodiments, when the command member is in the second release angular position the protruding element is housed in the seat. The housing of the protruding element in the abovementioned seat thus allows not only the shift of the pushing member from the first service position to the second service position and therefore the extraction of the injection needle from the device, but also the transfer of the rotary motion from the command member to the pushing member when the pushing member is in the second service position and the release of the support member by the pushing member, with the consequent retraction of the injection needle inside the device.

In some embodiments, the device of the disclosure comprises a motion transmission member configured to activate the shift of the injection needle movement mechanism from the first operating configuration to the second operating configuration. The motion transmission member can be activated automatically and can transmit the motion also to other members of the device.

In some embodiments, the command member comprises a coupling portion coupled to the motion transmission member. The transfer of the motion from the motion transmission member to the command member therefore takes place through a mechanical coupling.

In some embodiments, the motion transmission member comprises a rack—endless screw coupling. In this way, a rotation of the endless screw causes the movement of the rack.

In certain embodiments, the command member comprises a toothing engaged to the endless screw. In this way, the rotation of the endless screw causes a rotation of the command member.

In some embodiments, the fluidic path comprises a flexible tube having a first end associated with the piercing needle and a second end associated with the injection needle. The flexibility of the tube allows it to be properly housed inside the device, even in small spaces, and allows the fluid communication between the piercing needle and the injection needle to be maintained despite the movement of the piercing needle following the opening of the fluidic path.

In some embodiments, the device comprises a motion transmission member configured to activate the movement of the driving member. The opening of the fluidic path is therefore a consequence of a movement of the motion transmission member, which once moved transmits the motion to the driving member and therefore to the support member of the piercing needle.

In some embodiments, the driving member comprises a first coupling portion configured to couple to the motion transmission member and a second coupling portion configured to couple to the support member. The transfer of the motion from the motion transmission member to the support member of the piercing needle therefore takes place due to a mechanical coupling between the motion transmission member and the driving member and between the driving member and the support member of the piercing needle.

In some embodiments, the driving member comprises a base body.

In certain embodiments, the first coupling portion and the second coupling portion extend on opposite sides from the base body. This expedient allows to spatially and functionally separate the portion of the driving member intended to receive the motion from the motion transmission member from the one intended to impart the motion to the support member, to the benefit of the functionality and structural simplicity of the fluidic path opening system and, therefore, also of the production cost and purchase cost of the device.

In some embodiments, the motion transmission member comprises a rack.

In certain embodiments, the first coupling portion comprises a toothing engaged to the rack. In this way, the movement of the rack causes a rotation of the driving member.

In some embodiments of the device of the present disclosure, the second coupling portion comprises a perimeter wall provided with a through opening.

In some embodiments, the support member comprises an abutment element configured to be in abutment against an outer surface of the perimeter wall when the driving member is in the first angular position and at the through opening when the driving member is in the second angular position.

In some embodiments, the abutment element has a size such that it can pass through the through opening.

The opening of the fluidic system therefore takes place through an effective and reactive mechanical coupling. Until, during the rotation of the driving member, the abutment element of the support member of the piercing needle remains in abutment against the perimeter wall of the driving member, the piercing needle remains in a position distal from the pierceable septum and the fluidic path remains closed. When, during the rotation of the driving member, the through opening is in a position facing the abutment element, the pushing action exerted on the support member of the piercing needle by the elastic element moves the support member toward the pierceable septum until the piercing needle pierces the pierceable septum, thereby opening the fluidic path.

In some embodiments, the driving member is movable until it reaches a third angular position in which the driving member prevents the support member from moving from the second operating position to the first operating position. In this way, it is avoided that the support member accidentally returns to its first operating position, i.e. that the piercing needle exits the container during the delivery of the therapy, with consequent undesired closure of the fluidic path. This could for example occur in the event that the residual thrust exerted by the elastic element on the support member after the piercing needle has pierced the pierceable septum were not sufficient to keep the piercing needle inside the container during the delivery of the therapy or in the event of malfunction or failure of the elastic element.

In some embodiments, the perimeter wall delimits in the driving member an area configured to receive the abutment element when the driving member is in the second angular position.

In some embodiments, when the driving member is in the third angular position the abutment element is at an inner surface of the perimeter wall. In this condition, the abutment element is surrounded by the perimeter wall of the driving member and it is prevented any accidental and undesired movement of the abutment element up to its initial position, which would cause the exit of the piercing needle from the container and, consequently, the closure of the fluidic path.

In some embodiments, the support member comprises a main body.

In certain embodiments, the abutment element protrudes from the main body.

In some embodiments, the elastic element is a torsion spring comprising a plurality of coils arranged around an axis parallel to the rotation axis.

In some embodiments, the coils of the torsion spring are arranged around an axis orthogonal to the rotation axis.

In some embodiments, the torsion spring can be arranged in such a way that the thrust exerted by the torsion spring on the support member is sufficient to keep the piercing needle inside the container during the delivery of the therapy, without therefore the need to provide for the expedients discussed above to avoid an accidental and undesired return of the support member to the first operating position.

In some embodiments, the device has a reversible initial configuration in which the stop element is in a distal position with respect to the locking element and the locking element is movable integrally with the shielding element from the first operating position to the second operating position and vice versa. The shielding element is then free to move between the first operating position and the second operating position before applying the device on the skin of the patient.

In some embodiments, the device has an irreversible final configuration in which the stop element and the locking element are in mutual contact and the shielding element is locked in the first operating position.

In some embodiments, when the device is in the reversible initial configuration the injection needle is in the rest position. The injection needle movement mechanism is therefore deactivated and a possible exit of the injection needle outside the device can only occur following a malfunction of the abovementioned injection needle movement mechanism or a voluntary or accidental activation of the device by the user. Under these circumstances, however, the tip of the injection needle is covered by the shielding element, which is in its extracted position.

In some embodiments, when the device is in the irreversible final configuration the injection needle is in the rest position. If the injection needle is accidentally in the injection position and the device is not in contact with the skin of the patient, for example because it was accidentally or voluntarily removed from the skin of the patient before the end of the delivery of the therapy, the shielding element immediately comes out and covers the tip of the injection needle.

In some embodiments, the stop element is movable from an initial position in which the stop element and the locking element are not superimposed on each other to a final position in which the stop element and the locking element are superimposed on each other. Until the stop element reaches the final position, the shielding element remains free to move from the first operating position to the second operating position and vice versa. When the stop element reaches the final position, the shielding element exits the device and covers the tip of the injection needle if the injection needle is in the injection position.

In some embodiments, the stop element is movable from the initial position to the final position along a first direction.

In some embodiments, the locking element is movable integrally with the shielding element between the first operating position and the second operating position along a second direction orthogonal to the first direction.

In some embodiments, when the device is in the reversible initial configuration the stop element is movable along the first direction and the device switches from the reversible initial configuration to the irreversible final configuration when the stop element is in the final position and the locking element moves along the second direction from the second operating position to the first operating position passing beyond the stop element.

In some embodiments, one of the locking element or the stop element is made of a rigid material and the other one of the locking element or the stop element is made of a deformable material.

In some embodiments, the movement of the locking element along the second direction causes an interference between the locking element and the stop element and a deformation of the element made of a deformable material that is suitable to allow the passage of the element made of a rigid material.

In some embodiments, the locking element is made of a rigid material and the stop element is made of a deformable material.

In certain embodiments, the stop element can comprise a first surface facing the locking element when the stop element is in the final position and the locking element is in the second operating position, and a second surface facing on the opposite side of the first surface and toward the locking element when the stop element is in the final position and the locking element is in the first operating position.

In some embodiments, the first surface allows the stop element to deform due to the interference with the locking element and the locking element to move along the second direction from the second operating position to the first operating position.

In certain embodiments, the first surface is inclined with respect to a plane orthogonal to the second direction, thereby facilitating the passage of the locking element from one side to the other side of the stop element following the deformation of the latter.

In some embodiments, the second surface defines an undercut that prevents the locking element from moving from the first operating position when the device is in the irreversible final configuration.

In certain embodiments, the second surface is orthogonal to the second direction.

In some embodiments, the shielding element comprises a base provided with a through hole or with a pierceable septum to allow the passage of the injection needle during the movement of the injection needle between the rest position and the injection position when the shielding element is in the second operating position.

In some embodiments, the base comprises a raised edge which defines in the shielding element a recess configured to house the tip of the injection needle both when the shielding element is in the second operating position and the injection needle is in the rest position and when the shielding element is in the first operating position and the injection needle is in the injection position. The raised edge surrounds the tip of the injection needle and prevents the user from coming into contact with the tip if the injection needle is outside the device and the device is not applied on the skin of the patient.

In some embodiments, the device comprises a fluidic path opening system that can be activated to put the injection needle in fluid communication with the container. This system is activated shortly after the device is put into operation, which can be done for example by pressing a special button by the patient after having applied the device on the skin of the patient.

In some embodiments, the locking element is configured to lock the shielding element in the first operating position upon activation of the fluidic path opening system, and thus after the device has been removed from the skin of the patient, possibly even before the end of the delivery of the therapy.

In some embodiments, the fluidic path opening system comprises a piercing needle configured to pierce a pierceable septum coupled to an end of the container, a driving member configured to drive the movement of the piercing needle and a motion transmission member configured to drive the driving member.

In some embodiments, the stop element is associated with the motion transmission member. In this way, both the fluidic path opening system and the locking of the shielding element are driven by a single motion transmission member, with a consequent structural simplification of the device.

In some embodiments, the device comprises a position sensor configured to detect a contact of the device with the skin of the patient. Thanks to the abovementioned sensor, it is ensured that the device cannot be put into operation before being applied on the body of the patient or, in other words, it is ensured that the device can be put into operation only when it is effectively under the conditions of being able to deliver the medicament. This is particularly advantageous since the medicaments used in these devices are typically very expensive and that in order to ensure the safety of the patients, the device is considered to have been used immediately after it is put into operation, regardless of whether the medicament is then actually delivered to the patient or whether such a delivery is successful.

In some embodiments, the position sensor comprises a magnet integrally associated with the shielding element and a Hall effect sensor arranged in the device close to the magnet. In this way, the detection of the contact between the device and the body of the patient takes place, after the magnet approaches the Hall effect sensor, due to the movement of the shielding element from outside to inside the device as soon as the device is applied on the body of the patient.

In some embodiments, the magnet is entirely housed in a seat formed in the shielding element.

In some embodiments, the locking element is associated with the magnet.

In some embodiments, the shielding element comprises a base provided with a through hole to allow the passage of the injection needle during the movement of the injection needle between the rest position and the injection position.

In some embodiments, the base comprises a raised edge which defines in the shielding element a recess that houses the tip of the injection needle both when the shielding element is in the second operating position and the injection needle is in the rest position and when the shielding element is in the first operating position and the injection needle is in the injection position. The raised edge surrounds the tip of the injection needle and prevents the user from coming into contact with the tip if the injection needle is outside the device and the device is not applied on the skin of the patient.

In some embodiments, the flexible sleeve is integrally associated with the base.

In some embodiments, the flexible sleeve is defined by a membrane having an inner surface that is integrally associated with the outer surface of the base.

In some embodiments, the membrane is of the bellows type and has a substantially conical or truncated conical shape. In this way the membrane can be telescopically folded inside the device when the device is applied on the skin of the patient, thus occupying an extremely limited space, to the benefit of the compactness of the device.

In certain embodiments, the flexible sleeve is not configured to close the through hole of the base of the shielding element. In such a case, the through hole is closed tightly by a pierceable septum configured to be pierced by the injection needle when the injection needle moves from the rest position to the injection position.

In some embodiments, the flexible sleeve has a base surface integrally associated with the base of the shielding element.

In certain embodiments, the base surface of the flexible sleeve covers the through hole of the base of the shielding element and is pierceable by the injection needle when the injection needle moves from the rest position to the injection position. In this case the flexible sleeve covers with continuity the shielding element also covering the through opening of the device through which the injection needle exits and it is the same injection needle that pierces the base surface of the flexible sleeve when it comes out from the shielding element and, thus, from the flexible sleeve. It is therefore not necessary to worry about compensating for any dimensional differences between the through hole and the septum. Furthermore, in this case the flexible sleeve, in addition to ensuring the tightness at the through hole created by the injection needle, retains within the device any drops of drug released by the device before the delivery of the medicament.

In some embodiments, the flexible sleeve is entirely arranged within the device when the shielding element is in its second operating position, so as not to be cumbersome when the device is applied on the skin of the patient.

In some embodiments, the device comprises a compression ring welded to an application surface of the device at the through opening.

In some embodiments, the flexible sleeve comprises an annular end portion which is interposed between the application surface and the compression ring. The latter thus firmly constrains by compression the flexible sleeve to the device. Consequently, the desired tightness at the through opening of the device is obtained due to the compression of the annular end portion on the application surface of the device by the compression ring.

In some embodiments, the compression ring is welded by ultrasonic welding.

In some embodiments, the flexible sleeve is made of a silicone material for medical use.

In some embodiments, the first motion transmission member is configured to activate the fluidic path opening system when the rotor rotates in the first rotation direction for a first time interval.

In some embodiments, the first motion transmission member is configured to activate the injection needle movement mechanism when the rotor rotates in the first rotation direction for a second time interval.

In some embodiments, the second time interval is subsequent to the first time interval.

Therefore, the first motion transmission member can at first open the fluidic path and subsequently cause the extraction of the injection needle from the device. The execution of two operation phases can be therefore temporarily separated despite being driven by the same motion transmission member.

In some embodiments, the device comprises a shielding element movable between a first operating position in which the shielding element protrudes from the device and a second operating position in which the shielding element does not protrude from the device. This shielding element allows to protect the patient from accidental contacts with the injection needle when the device is not applied on the skin of the patient, if the injection needle is outside the device.

In some embodiments, it is provided that the shielding element is in the first operating position before applying the device on the skin of the patient and covers the injection needle if for some reason the latter is outside the device. In fact, although it is provided that before applying the device on the skin of the patient the injection needle is inside the device, it cannot be ruled out that because of a malfunction or failure of the injection needle movement mechanism it comes out of the device.

The device can further comprise a stop mechanism configured to stop the movement of the shielding element.

In certain embodiments, the stop mechanism comprises a stop element and the shielding element comprises a locking element configured to cooperate with the stop element and to lock the shielding element in the first operating position when the device is removed from the skin of the patient. In this way, if the injection needle remains outside the device at the end of the delivery of the therapy or if the device is accidentally or voluntarily removed from the skin of the patient before the end of the delivery of the therapy, the shielding element immediately exits the device and remains locked in the extracted position, preventing also in this case the patient from being able to come into contact with the injection needle.

In some embodiments, the first motion transmission member is configured to drive the stop mechanism when the rotor rotates in the first rotation direction for a given time interval. The locking of the shielding element once the device is removed from the skin of the patient is therefore carried out by the same motion transmission member that is used to open the fluidic path and to extract the injection needle, to the benefit of the f production and purchase costs of the device.

In some embodiments, the given time interval coincides at least in part with the second time interval.

In certain embodiments, the abovementioned given time interval coincides exactly with the second time interval. The activation of the stop mechanism of the shielding element therefore takes place simultaneously with the activation of the injection needle movement mechanism, so as to be sure that in the event that the device is removed from the skin of the patient before the end of the delivery of the therapy, the shielding element, once exited from the device, remains locked in position outside the device.

Alternative embodiments are however foreseen wherein the abovementioned given time interval is subsequent to the second time interval.

In some embodiments, the first motion transmission member comprises a rack movable along a first direction and an endless screw coupled to the rack.

In some embodiments, the endless screw is coupled to a command member which controls the injection needle movement mechanism.

In some embodiments, the rack comprises a first coupling portion configured to drive a driving member of the fluidic path opening system during the movement of the rack along the first direction.

In some embodiments, the rack comprises a second coupling portion arranged upstream with respect to the first coupling portion along the first direction and coupled to the endless screw.

The rotation of the endless screw can cause the extraction of injection needle from the device and the motion of the rack along the first direction. This motion can cause the opening of the fluidic path.

In some embodiments, the stop element is associated with a third coupling portion of the rack arranged upstream with respect to the first coupling portion along the first direction.

In some embodiments, the third coupling portion is interposed between the first coupling portion and the second coupling portion. It is therefore ensured that when the device is removed from the skin of the patient and the shielding element exits the device it remains immediately locked in position outside the device.

In some embodiments, after driving the medicament delivery mechanism by the second motion transmission member by rotating the rotor in the second rotation direction for the fourth time interval, the injection needle movement mechanism is driven by the first motion transmission member by rotating the rotor in the first rotation direction for a fifth time interval, causing the movement of the injection needle from the injection position to the rest position.

In some embodiments, after activating the fluidic path opening system by the first motion transmission member by rotating the rotor in the first rotation direction for the first time interval and before removing the device from the skin of the patient, the stop mechanism of the shielding element is driven by the first motion transmission member by rotating the rotor in the first rotation direction for a given time interval.

In some embodiments, the given time interval coincides at least in part with the second time interval.

In some embodiments, both activating the fluidic path opening system and driving of the stop mechanism of the shielding element comprise moving the rack along the first direction.

In some embodiments, the device comprises a position sensor configured to detect a contact of the device with the skin of the patient. Thanks to the abovementioned sensor, it is ensured that the device cannot be put into operation before being applied on the body of the patient or, in other words, it is ensured that the device can be put into operation only when it is effectively under the conditions of being able to deliver the medicament. This is particularly advantageous since the medicaments used in these devices are typically very expensive and that in order to ensure safety conditions of the patients, the device is considered as having been used immediately after it is put into operation, regardless of whether the medicament has been actually delivered to the patient or whether such a delivery is successful.

In some embodiments, the device comprises a delivery module and a control module which are mutually couplable and decouplable.

In some embodiments, the delivery module is disposable while the control module is reusable.

In some embodiments, the rotor comprises a driving rotor and a magnetic rotor.

In some embodiments, the delivery module comprises the magnetic rotor, the cartridge, the fluidic path, the fluidic path opening system, the injection needle movement mechanism, the medicament delivery mechanism, the first motion transmission member, the second motion transmission member, while the control module comprises the driving rotor, a drive motor for driving the driving rotor and the control unit.

The shielding element, if provided, is associated with the delivery module.

The position sensor, if provided, can comprise a magnet housed in the delivery module and a Hall effect sensor housed in the control module.

In some embodiments, the magnet is integrally associated with the shielding element.

In some embodiments, the delivery module comprises an ignition magnet.

In some embodiments, the control module comprises a power switch for powering the control unit.

In some embodiments, the device is put into operation by the patient by pressing a special specific activation button.

In some embodiments, the activation button is arranged on the control unit.

In some embodiments, the control module comprises a plurality of electronic components and a hardware unit that powers the electronic components. Therefore, before being put into operation the device is in a sleep mode.

In some embodiments, the control module comprises an NFC Tag on which a plurality of information is stored.

In some embodiments, before putting the device into operation, the delivery module and the control module are coupled to each other. This coupling causes the control unit to be switched on due to the fact that the ignition magnet, being close to the power switch which powers the control unit, triggers it.

In some embodiments, after switching on, the control unit performs a self-diagnosis.

In some embodiments, after switching on, the control unit queries the NFC Tag by reading the information stored therein. In particular, the control unit performs any one or all of the following actions: check if the delivery module has already been used, check if the delivery module is configured to deliver a correct dosage of the medicament, establish the method of delivery of the medicament, establish the speed of delivery of the medicament.

In some embodiments, after switching on the control unit reads the signal of the position sensor to establish if the device is in contact with the skin of the patient.

In some embodiments, if the control unit does not detect the signal of the position sensor within a predetermined time, the control unit switches off. The device thus returns to the sleep mode.

BRIEF DESCRIPTION OF THE DRAWINGS

Further features and advantages of the present disclosure will become clearer from the following detailed description of preferred embodiments thereof, made with reference to the accompanying drawings and given for indicative and non-limiting purpose. In such drawings.

DETAILED DESCRIPTION

Figure 1:
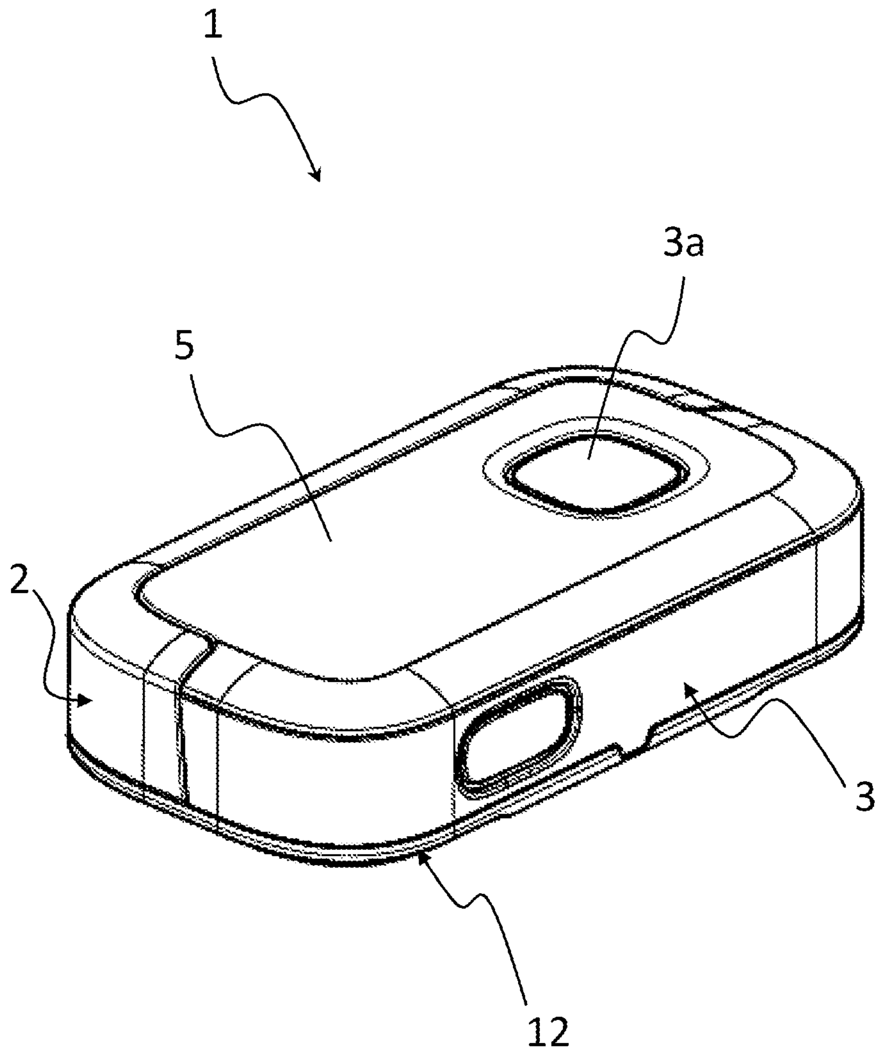
FIG. 1 is a perspective view of an example device according to the present disclosure.

In FIG. 1, an example wearable type device for the subcutaneous delivery of a medicament in accordance with the present disclosure is indicated with 1. The application of the device on the body of the patient is carried out by a user, for example a doctor or a nurse or the patient.

Figure 2:
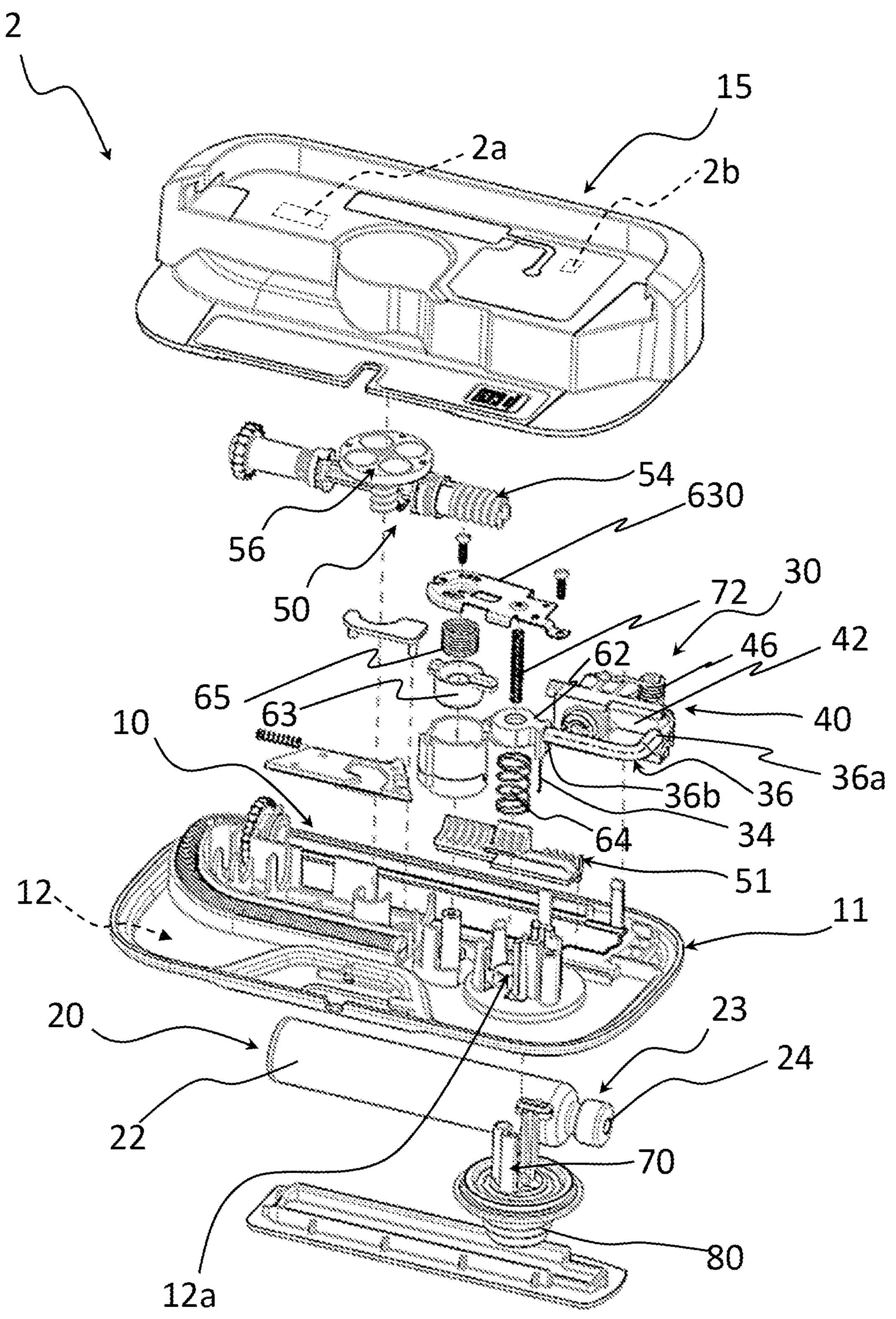
FIG. 2 is an exploded perspective view of a first embodiment of a module of the device of FIG. 1.
Figure 3:
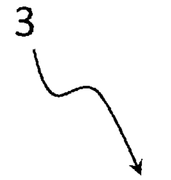
FIG. 3 is an exploded perspective view of another module of the device of FIG. 1.
Figure 3:
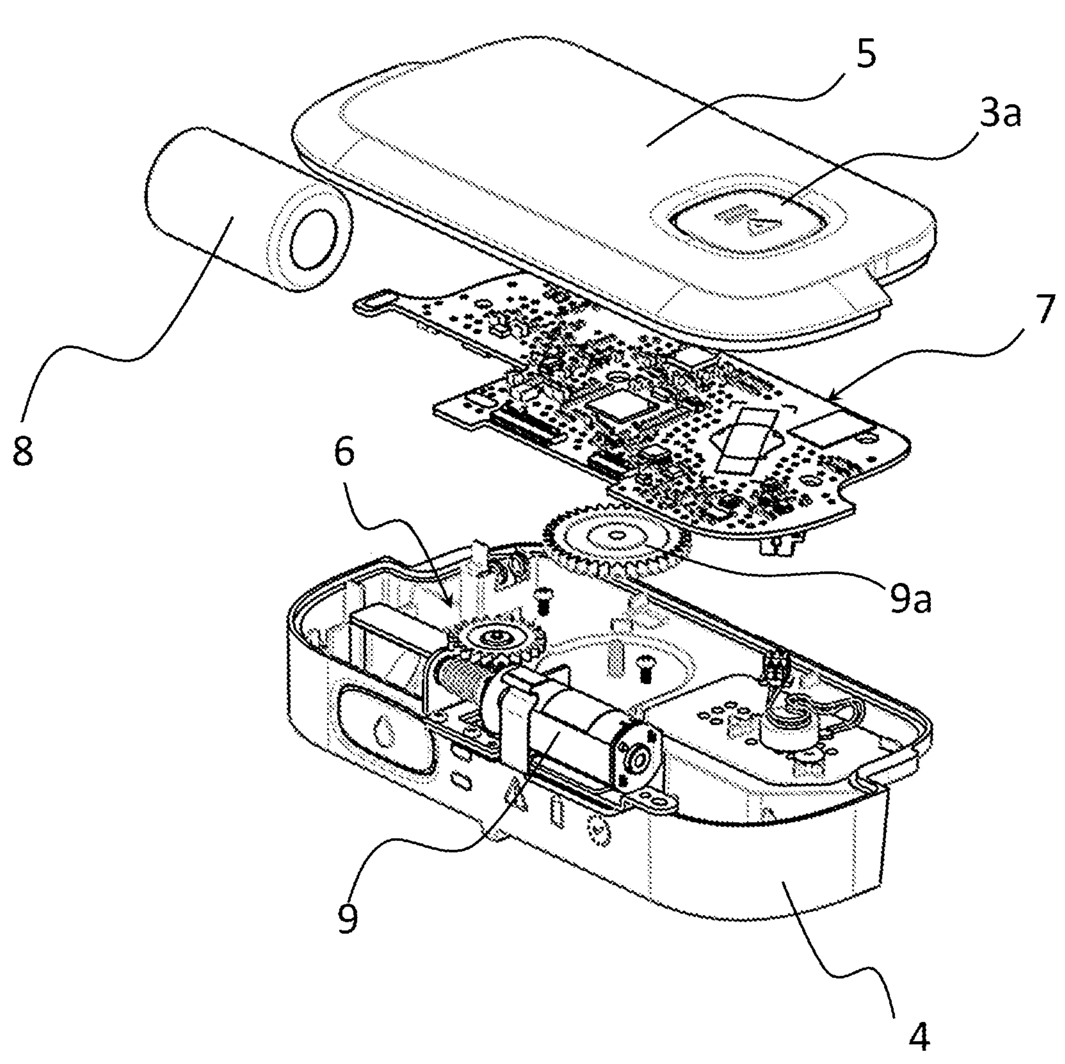

The device 1 comprises a delivery module 2, shown in FIG. 2, and a control module 3, shown in FIG. 3.

The device 1 is obtained by mutually coupling the delivery module 2 and the control module 3. This coupling is reversible, i.e. the two modules 2 and 3 can be decoupled after having been coupled.

One or more gaskets are interposed between the delivery module 2 and the control module 3 in order to ensure the tightness of the mutual coupling.

The delivery module 2 is, in some instances, disposable, while the control module 3 is, in some instances, reusable. In other words, the delivery module 2 is configured to be applied on the body of the patient only once and for a certain period of time to deliver the medicament, completely or in part, in one or more subsequent injections, even temporally spaced apart from each other. Conversely, the control module 3 can be used several times, by coupling it from time to time with a new delivery module 2.

As shown in FIG. 3, the control module 3 comprises a lower body 4 and an upper cover 5 associated with the lower body 4, for example, by ultrasonic welding. In this case ultrasonic welding is preferable to laser welding because the latter requires the use of transparent materials that are not considered convenient to be used for the control module 3 since it can be customized with different colours and/or finishes.

A housing compartment 6 is defined between the lower body 4 and the upper cover 5. The housing compartment 6 contains a control unit 7, usually made of a printed circuit and configured to control the delivery of the medicament from the delivery module 2, a power supply battery 8 configured to power the control unit 7 and a motor 9 that drives in rotation a driving magnetic rotor 9*a*.

A plurality of electronic components and a hardware unit that powers the electronic components are provided in the control module 3.

The control module 3 further comprises a switch configured to power the control unit 7 and an activation button 3*a*. The patient operates the device 1 by pressing the activation button 3*a*.

As shown in FIG. 2, the delivery module 2 comprises a main body 11 and an intermediate cover 15 associated with the main body 11 and interposed between the main body 11 and the lower body 4 of the control module 3. In some instances, the intermediate cover 15 is welded to the main body 11 by laser welding. In this case the latter is preferable to an ultrasonic welding because the assembly of the delivery module 2 takes place with all the members described below already mounted on the main body 11 and the use of an ultrasonic welding would risk activating these members.

A housing compartment 10 is defined between the main body 11 and the intermediate cover 15.

Figures 10, 11:
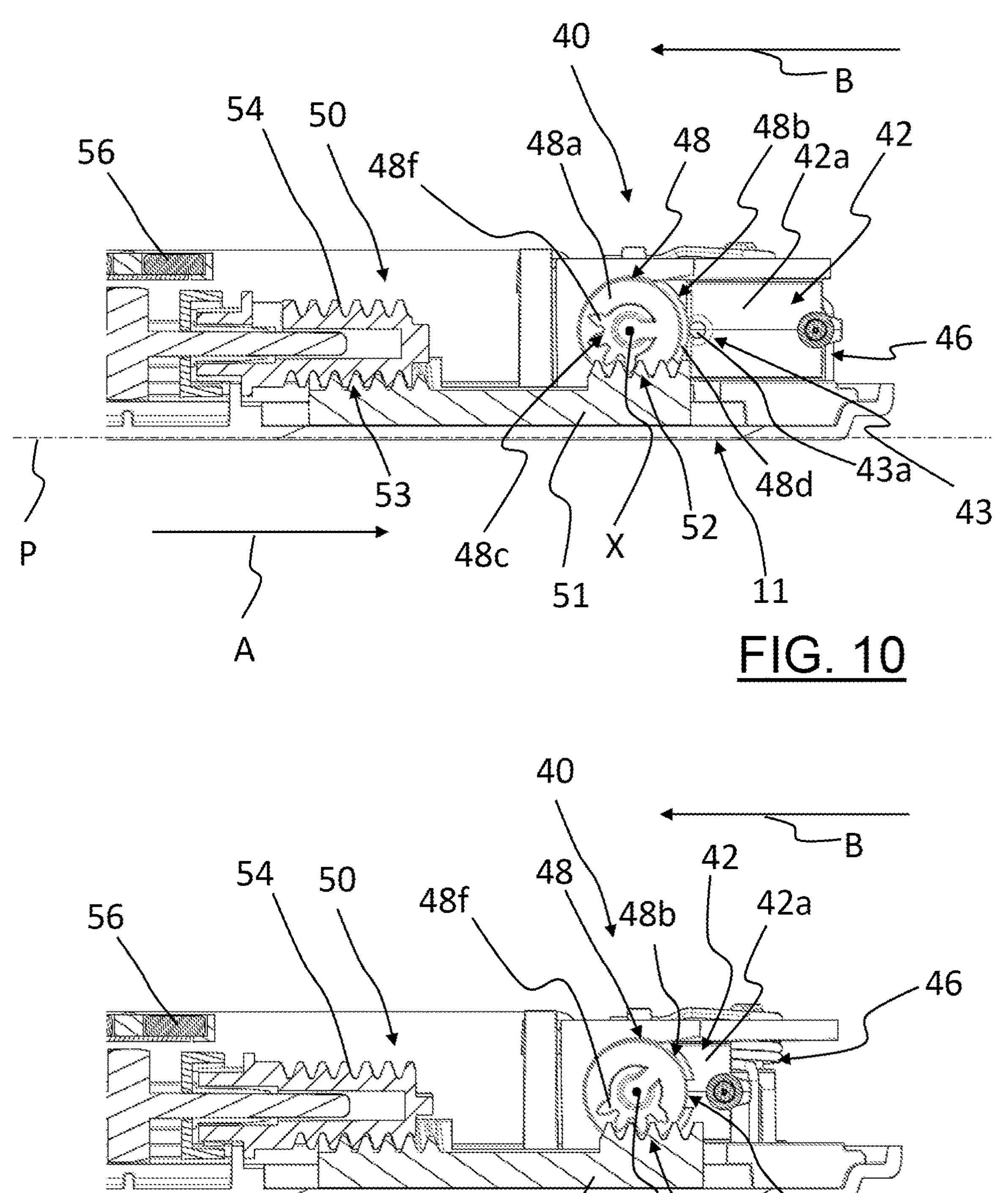
FIG. 10 is a sectional side view of a portion of the module of FIG. 6 in an initial configuration of the device of FIG. 1.
FIG. 11 is a sectional side view of the portion of FIG. 10 in an operating configuration of the device subsequent to that of FIG. 10 and corresponding to that of FIG. 9.

As shown in FIG. 10, the main body 11 comprises an application surface 12 configured to come into contact with the body of the patient. The application surface 12 is substantially flat and defines a plane P for resting on the skin of the patient.

The application surface 12 comprises a through opening 12*a* (FIG. 2).

With reference again to FIG. 2, the housing compartment 10 is configured to house a plurality of components, including a cartridge 20 and a fluidic path 30. In the present description, the term "fluidic path" is used to indicate any element or assembly of elements that is configured to be connected, at a first end thereof, to the cartridge housed inside the delivery device and comprising, at an end thereof opposite to the abovementioned first end, an injection needle intended to be inserted into the body of the patient to allow the transfer of the medicament from the cartridge to the body of the patient.

The delivery module 2 further comprises an ignition magnet 2*a* and an NFC Tag 2*b* on which a plurality of information is stored.

The cartridge 20 is arranged on the main body 11 and comprises a substantially cylindrical container 22, made of a plastic or glass material and containing the medicament to be delivered to a patient. A pierceable septum 24 that closes the container 22 and guarantees its sterility until the device 1 is used is provided at one end 23 of the container 22. A plunger 26 (shown in FIG. 6) is slidable in the container 22 to deliver the medicament.

Figure 6:
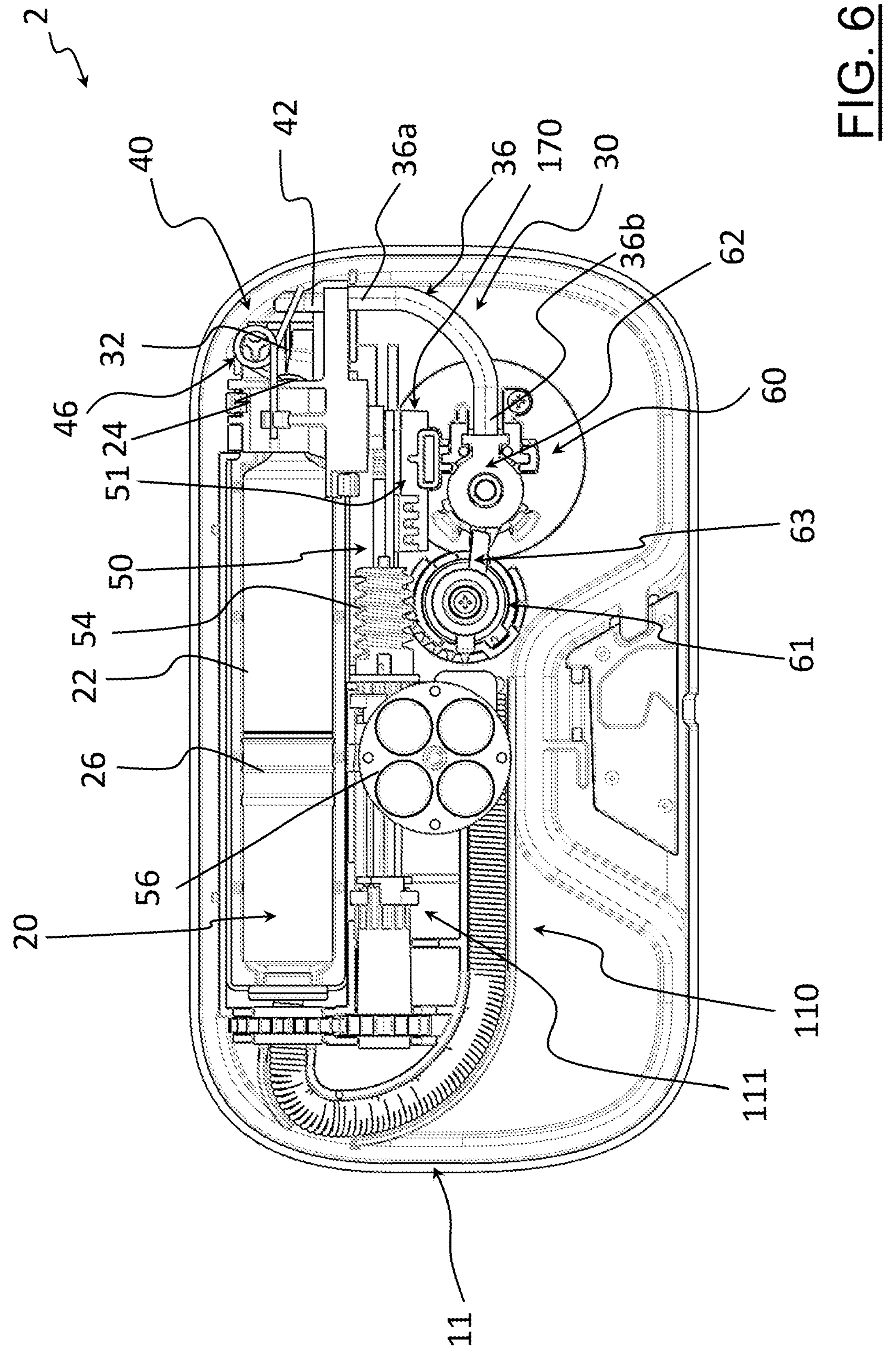
FIG. 6 is a sectional top view of the module of FIG. 2 in an initial configuration of the device of FIG. 1.

As shown in FIG. 6, the fluidic path 30 is also arranged on the main body 11 and is configured to be travelled by the medicament during the subcutaneous delivery of the medicament, allowing the transfer of the medicament from the cartridge 20 to the body of the patient.

The fluidic path 30 comprises a piercing needle 32 configured to pierce the pierceable septum 24 (as shown for example in FIG. 13), an injection needle 34 configured to be inserted into the body of the patient (as shown for example in FIG. 22), and a flexible tube 36 (shown for example in FIGS. 2 and 6) that puts the abovementioned needles 32 and 34 in fluid communication.

In particular, as shown in FIGS. 2 and 6, the flexible tube 36 has an end portion 36*a* connected to a support member 42 which supports the piercing needle 32 and an opposed end portion 36*b* connected to a support member 62 which supports the injection needle 34.

With reference to FIG. 6, the delivery module 2 further comprises a fluidic path opening system 40 configured to control the piercing of the pierceable septum 24 by the piercing needle 32 and thereby put the container 22 in fluid communication with the injection needle 34 through the piercing needle 32 and the flexible tube 36.

Figure 9:
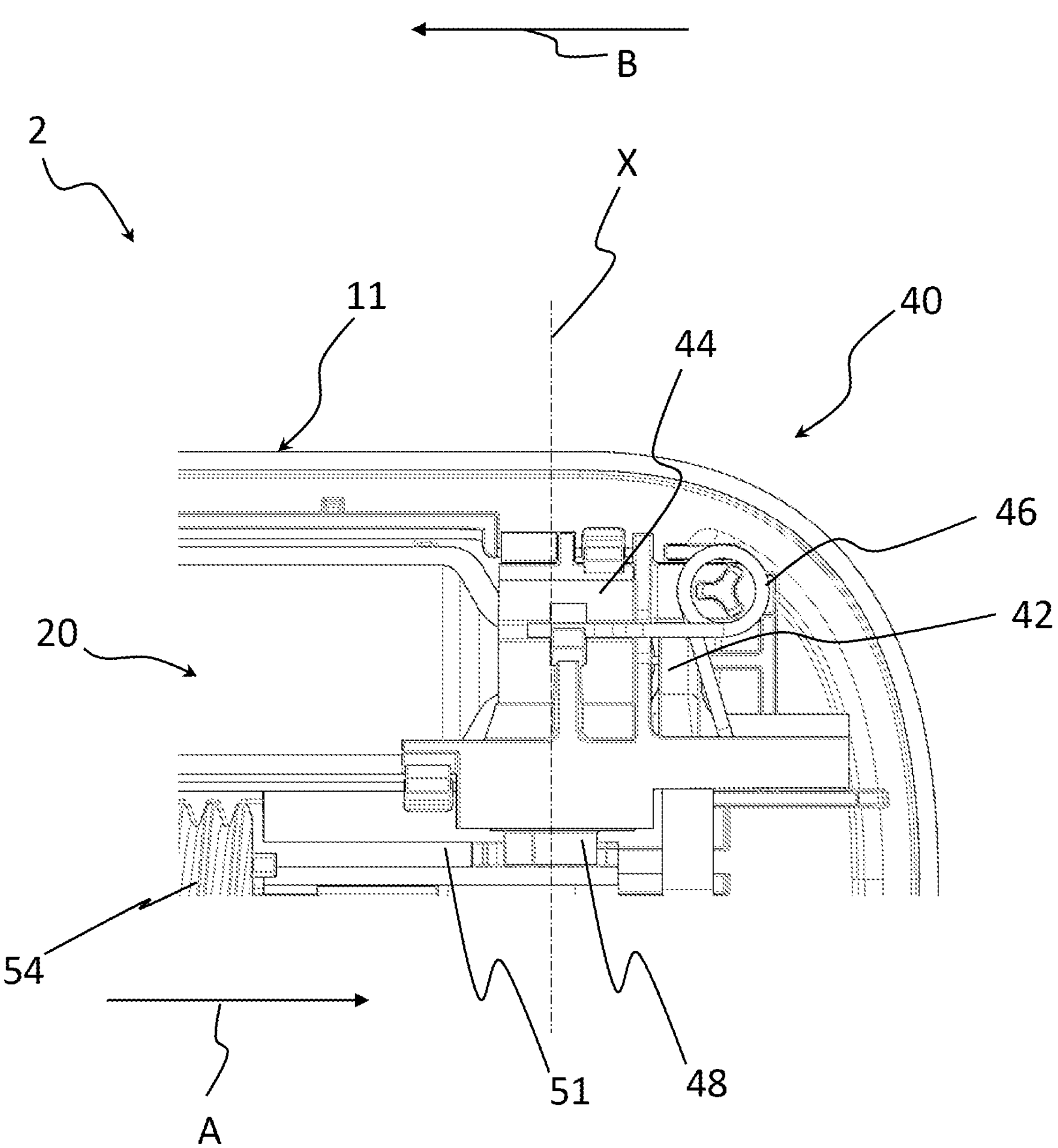
FIG. 9 shows an enlargement of a detail of the module of FIG. 6 in an operating configuration of the device subsequent to that of FIG. 6.
Figures 12, 13:
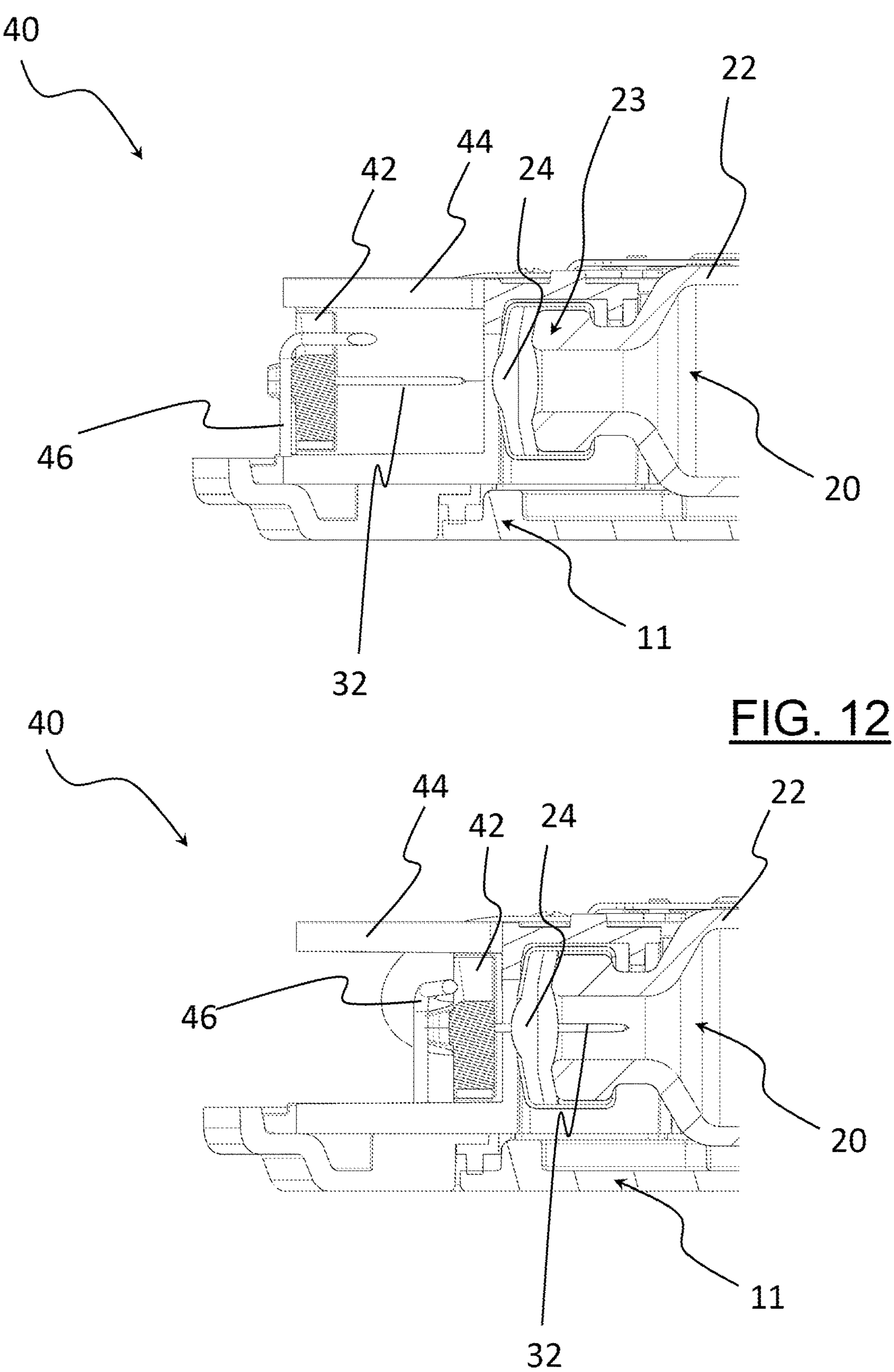
FIG. 12 is a sectional side view of another detail of the module of FIG. 6 in an initial configuration of the device of FIG. 1.
FIG. 13 is a sectional side view of the detail of FIG. 12 in an operating configuration of the device subsequent to that of FIG. 12 and corresponding to that of FIGS. 9 and 11.

The support member 42 is slidably mounted on a sliding guide 44 mounted on the main body 11 (FIGS. 9, 12 and 13). The support member 42 is movable between a first operating position in which the piercing needle 32 is spaced apart from the pierceable septum 24 (as shown for example in FIGS. 10 and 12) and the fluidic path 30 is closed, and a second operating position in which the piercing needle 32 has pierced the pierceable septum 24 (as shown for example in FIGS. 11 and 13) thereby opening the fluidic path 30.

With reference to FIGS. 10 and 11, the movement of the support member 42 is achieved thanks to the provision of a motion transmission member 50 comprising an endless screw 54 engaged to a rack 51 at a coupling portion 53 of the rack 51. The latter in turn is coupled to a driving member 48 which is rotatable about a rotation axis X and couplable to the support member 42.

In particular, the driving member 48 comprises a substantially circular base body 48*a*, a coupling portion 48*b* configured to couple to the support member 42 and a coupling portion 48*c* at which a coupling portion 52 of the rack 51 is engaged. The coupling portion 52 is arranged downstream with respect to the coupling portion 53 along the direction A.

The coupling portions 48*b* and 48*c* extend from the base body 48*a* on axially opposite sides with respect to the rotation axis X.

Figure 14:
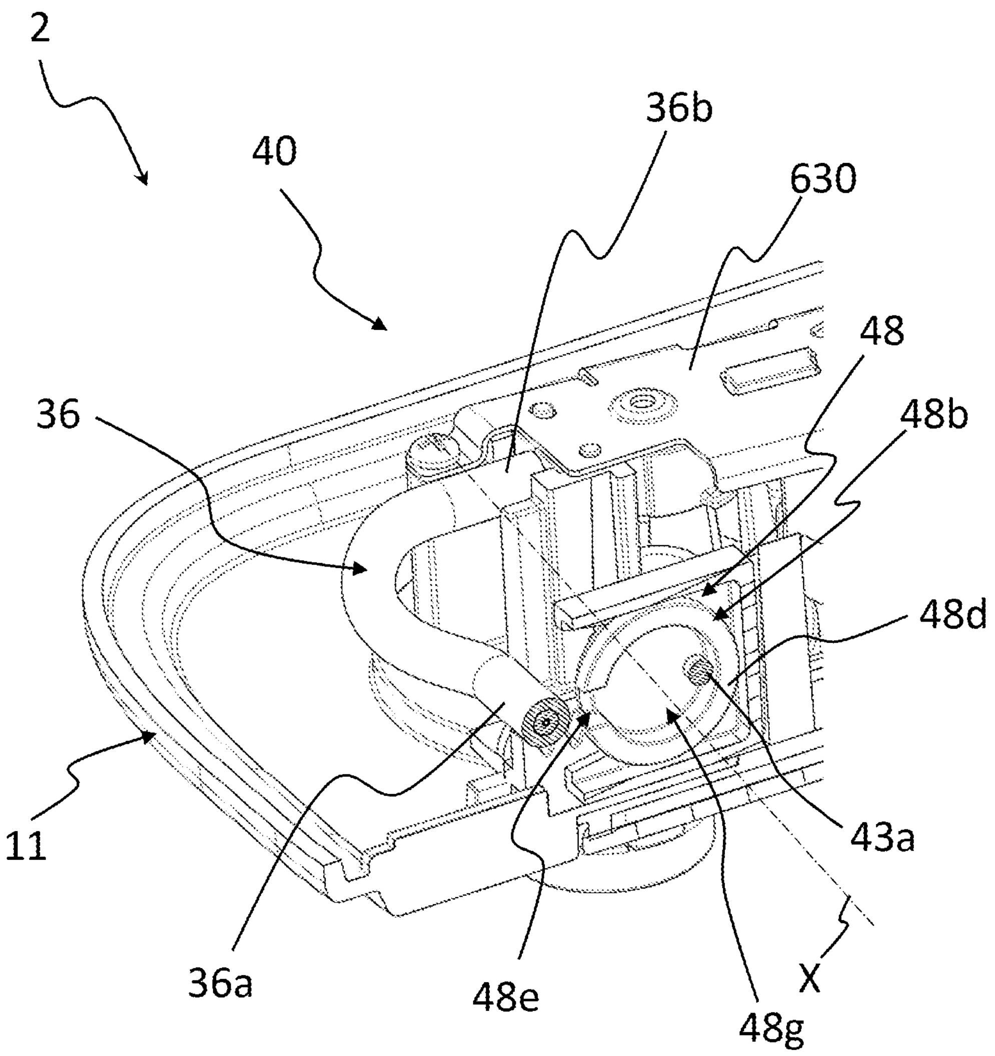
FIG. 14 is a perspective sectional view of some components of the module of FIG. 6 in an operating configuration of the device subsequent to that of FIG. 6 and corresponding to that of FIGS. 9, 11 and 13.

The coupling portion 48*b* is defined by a perimeter wall 48*d*. The latter is provided with a through opening 48*e* and delimits in the coupling portion 48*b* a substantially cylindrical area 48*g* (FIGS. 11 and 14).

The coupling portion 48*c* comprises a toothing 48*f* engaged to the coupling portion 52 of the rack 51 and extending circumferentially for a predetermined angle less than 360°, for example, less than 180°, such as equal to about 90°.

As shown in FIG. 10, the rack 51 is driven to move, toward the support member 42 along a direction A orthogonal to the rotation axis X and substantially parallel to the plane P, by the rotation of the endless screw 54 which in turn is driven to rotate by a magnetic rotor 56 (shown in full in FIG. 2) mounted on the main body 11 and driven by the driving magnetic rotor 9*a* provided in the control module 3. Due to the coupling between rack 51 and toothing 48*f*, the movement of the rack 51 causes the rotation of the driving member 48 about the rotation axis X.

As shown in FIG. 9, the support member 42 is subjected to a pushing action along a direction B opposite to the direction A by an elastic element 46, in particular a torsion spring. This spring comprises a plurality of coils arranged around an axis orthogonal to the rotation axis X and tends to push the support member 42 from the first operating position toward the second operating position.

As shown in FIGS. 10, 11 and 14, the support member 42 comprises a body 42*a* and an abutment element 43 protruding from the body 42*a* and sized so as to be able to pass through the through opening 48*e*. In particular, the abutment element 43 is defined by a cylindrical pin 43*a* which extends cantilevered from the outer side surface of the body 42*a*.

Until the driving member 48 rotates about the rotation axis X by an angle less than a predetermined value, the support member 42 remains in the first operating position due to the mutual abutment between the abutment element 43 and the outer surface of the perimeter wall 48*d*. This mutual abutment counteracts the pushing action exerted by the elastic element 46 on the support member 42 (FIG. 10).

As soon as the angle of rotation of the driving member 48 reaches the abovementioned predetermined value, the support member 42 is free to move from the first operating position to the second operating position along the direction B due to the fact that the abutment element 43 is at the through opening 48*e* (FIG. 11) and can pass through it due to the pushing action exerted by the elastic element 46, so as to arrange itself within the area 48*g* of the coupling portion 48*b* (FIG. 14).

Figures 15, 16:
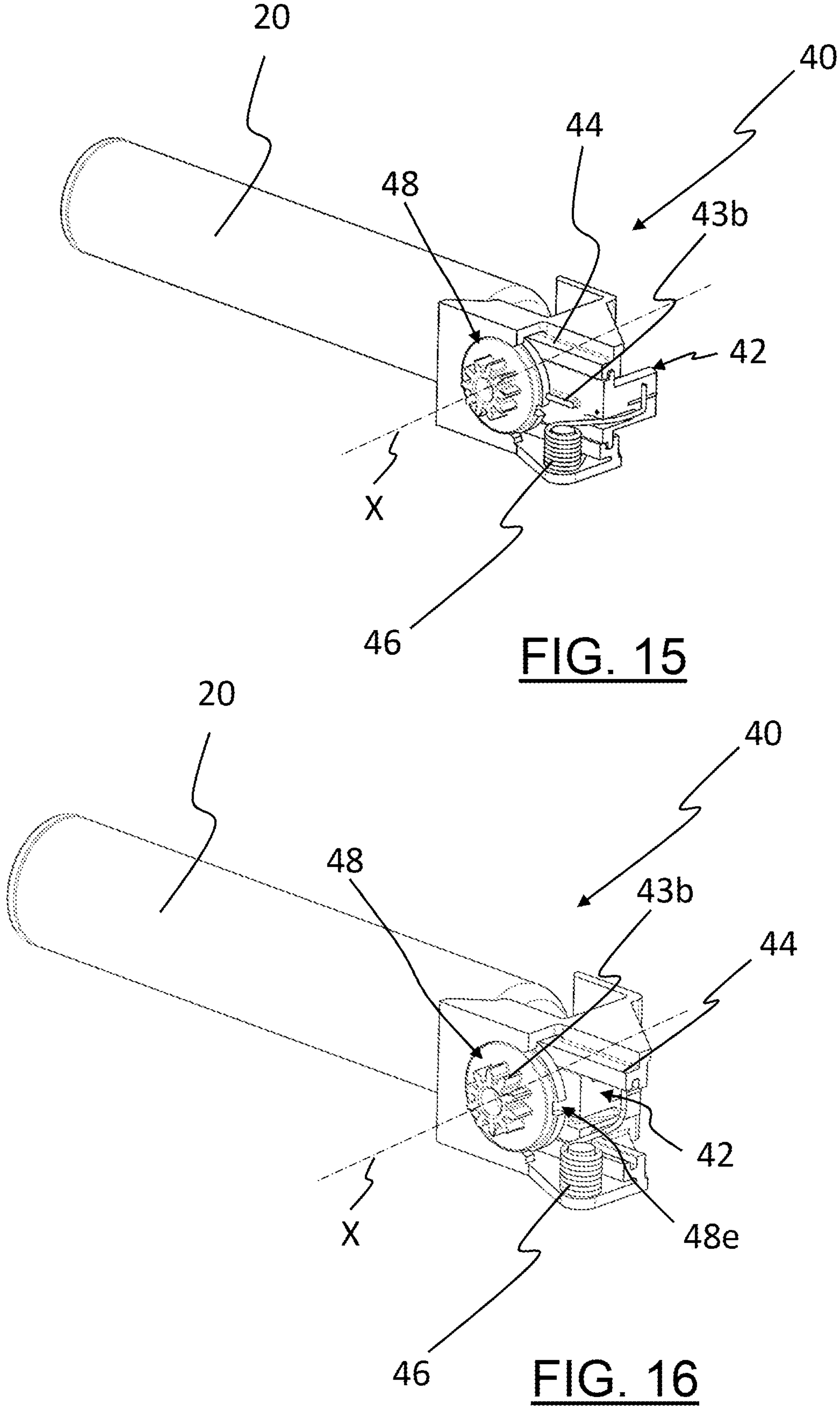
FIGS. 15 and 16 are perspective views of some components of a second embodiment of the device of the present disclosure in two subsequent operating configurations thereof.
Figure 17:
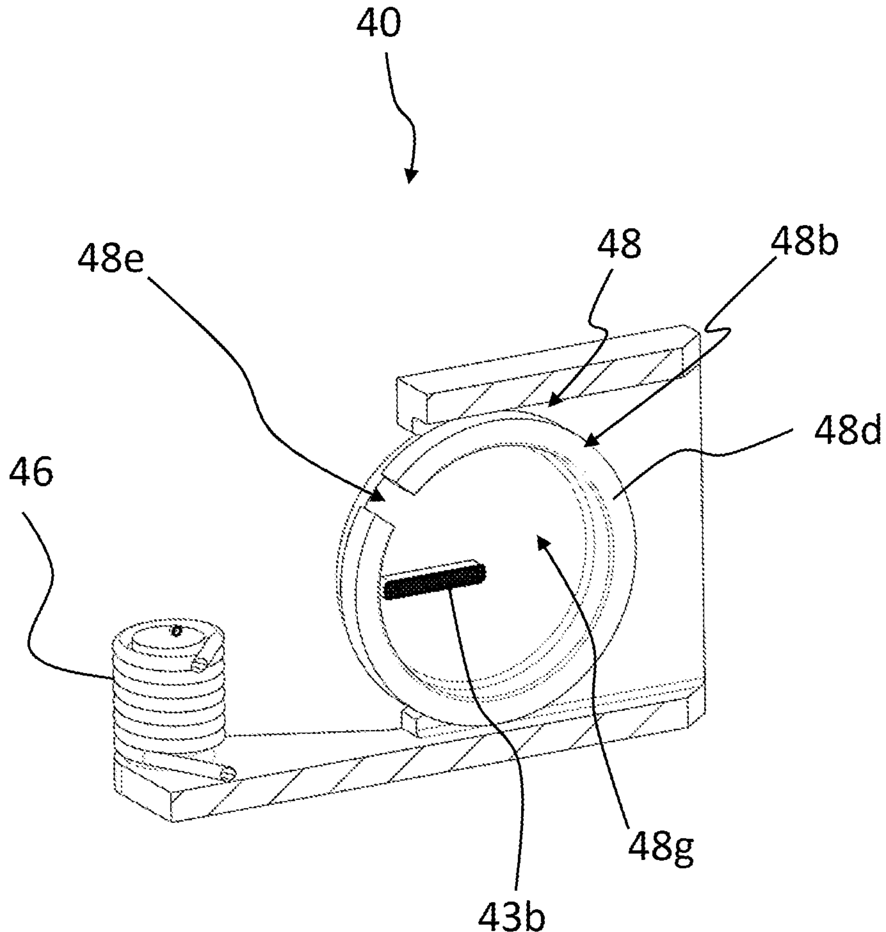
FIG. 17 is a perspective sectional view of some of the components of FIGS. 15 and 16 in an operating configuration of the device subsequent to that of FIG. 16.

FIGS. 15-17 show a second embodiment of the fluidic path opening system 40, which can also be used in the device 1 of the present disclosure as an alternative to the one described above. The elements of this second embodiment that are identical or equivalent to those described above are indicated with the same reference numeral.

In this second embodiment the coils of the torsion spring which defines the elastic element 46 are arranged around an axis orthogonal to the rotation axis X and positioned closer to the rack 51 with respect to the axis of the torsion spring of the embodiment described above.

Furthermore, in the embodiment of FIGS. 15-17, the abutment element 43 is defined by a straight rib 43*b* arranged on the outer side surface of the body 42*a*.

In FIG. 15 the driving member 48 is shown in a first angular position, while in FIG. 16 the driving member 48 is shown in a second angular position. These angular positions are functionally similar to those of FIGS. 10 and 11 of the first embodiment described above.

In FIG. 17 the driving member 48 is shown in a further angular position subsequent to that of FIG. 16. When the driving member reaches the angular position of FIG. 17 the rib 43*b*, previously entered into the area 48*g* of the coupling portion 48*b* (FIG. 16), is at an inner surface of the perimeter wall 48*d* and cannot exit the area 48*g*. In this way, the driving member 48 hinders a possible tendency of the support member 42 to move from the second operating position towards the first operating position.

Figure 20:
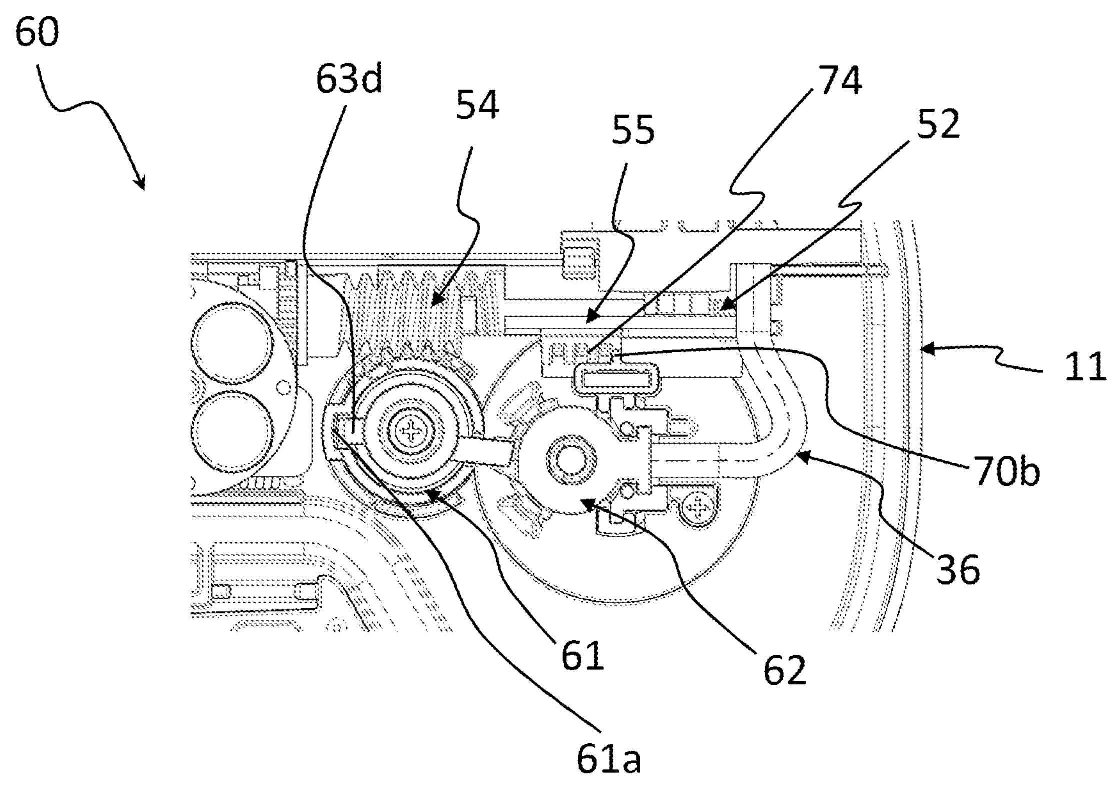
Figure 21:
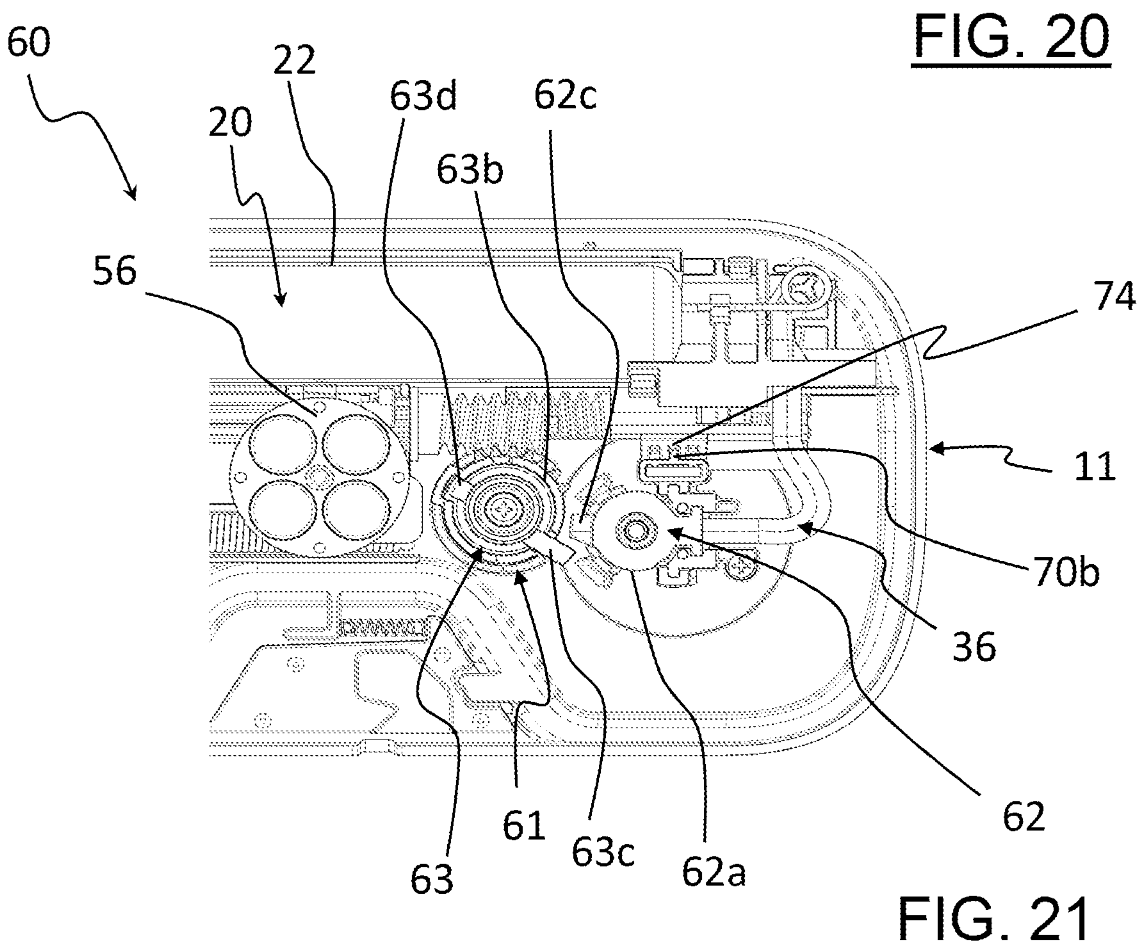

As shown in FIG. 6 and in FIGS. 18-23, the delivery module 2 also comprises an injection needle movement mechanism 60, configured to move the injection needle 34, at the beginning of the delivery of the therapy from a rest position, in which the injection needle 34 is entirely arranged inside the device 1 and does not protrude from the plane P of the device 1 (FIGS. 18 and 19), to an injection position in which the injection needle 34 protrudes at least partially from the plane P of the device 1 (FIGS. 20 and 22) through the through opening 12*a*, and at the end of the delivery of the therapy from the injection position to the rest position (FIG. 21).

The support member 62 which supports the injection needle 34 is movable orthogonally to the plane P between a first operating position in which the injection needle 34 is in the rest position and a second operating position in which the injection needle 34 is in the injection position.

The support member 62 has a substantially cylindrical shape and has an outer side surface 62*a* to which the end portion 36*b* of the flexible tube 36 is connected.

Figure 23:
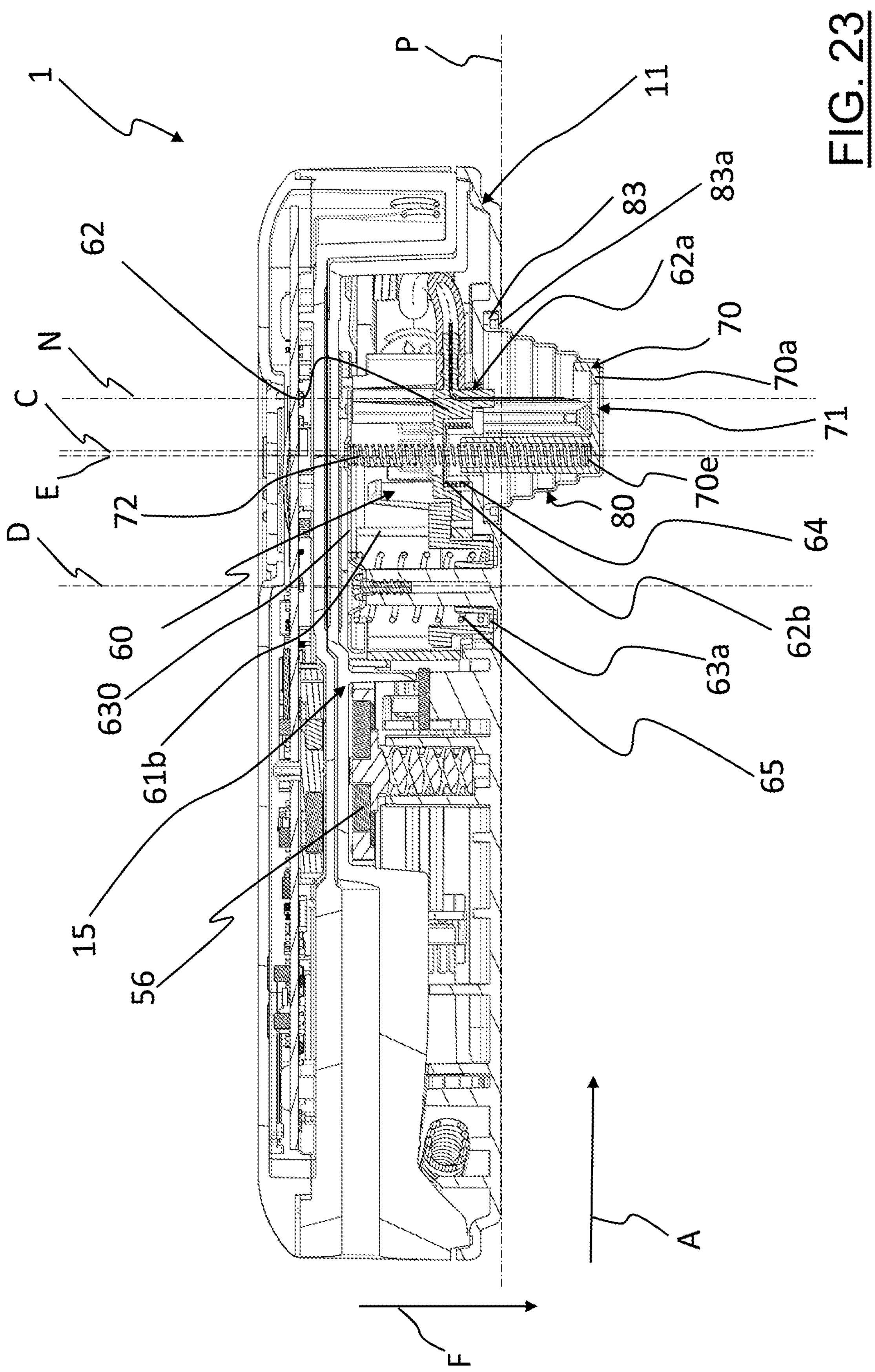
FIG. 23 is a sectional side view of the device of FIG. 1 in a possible operating configuration thereof in which the device is not applied on the skin of the patient.

As shown in FIG. 23, the support member 62 is subjected to a pushing action exerted by a compression spring 64. This pushing action tends to push the support member 62 towards its first operating position, so as to keep the injection needle 34 in the rest position before the use of the device 1 (FIG. 18) and to return the injection needle 34 to the rest position after the delivery of the therapy (FIG. 21).

In particular, the compression spring 64 is arranged between the main body 11 and an inner surface 62*b* of the support member 62 facing toward the plane P.

The compression spring 64 extends along an axis C orthogonal to the plane P, while the injection needle 34 extends along an axis N distinct from and parallel to the axis C. The axis N is arranged close to the outer side surface 62*a* of the support member 62.

With reference to FIGS. 18-23, the injection needle movement mechanism 60 comprises a pushing member 63 configured to move the support member 62 and, thus, the injection needle 34. The pushing member 63 is movable from a first service position (FIGS. 18 and 19) in which the support member 62 is in the first operating position and the injection needle 34 is in the rest position to a second service position (FIGS. 20, 22 and 23) in which the support member 62 is in the second operating position and the injection needle 34 is in the injection position.

Figure 22:
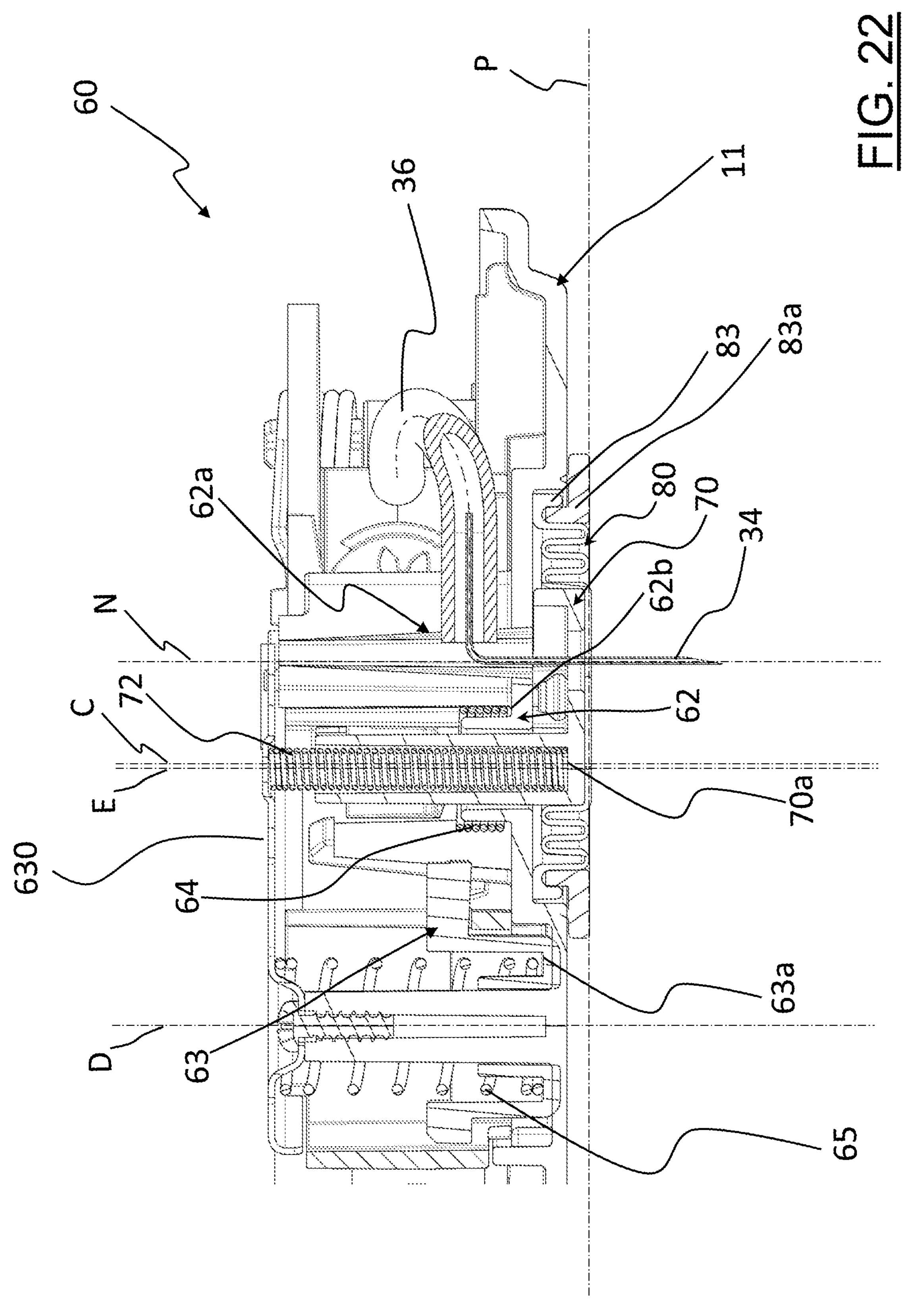
FIG. 22 is a sectional side view of a portion of the device of FIG. 1 in an operating configuration of the device subsequent to that of FIG. 8.

The pushing member 63 is subjected to a pushing action exerted by a compression spring 65 (FIGS. 22 and 23). This pushing action tends to push the pushing member 63 towards the second service position.

The compression spring 65 is arranged between the intermediate cover 15 and an inner surface 63*a* of the pushing member 63 facing away from the plane P.

The compression spring 65 extends along an axis D orthogonal to the plane P. The axis D is distinct from and parallel to the axis C and the axis N.

The compression spring 65 has an elastic constant greater than that of the compression spring 64.

The injection needle movement mechanism 60 has two main operating configurations.

In a first operating configuration, shown in FIG. 20, the pushing member 63 is coupled to the support member 62 and the force exerted by the compression spring 65 on the pushing member 63 moves it from the first service position to the second service position, moving the support member 62 from the first operating position to the second operating position. During the movement of the support member 62 the compression spring 64 is loaded.

In a second operating configuration, shown in FIG. 21, the pushing member 63 is decoupled from the support member 62 and the force exerted by the compression spring 64 on the support member 62 moves it from the second operating position to the first operating position. When the injection needle movement mechanism 60 is in the second operating configuration, the pushing member 63, being decoupled from the support member 62, remains in the second service position due to the pushing action exerted by the compression spring 65.

The pushing member 63 has a substantially cylindrical shape and is rotatably movable about the axis D from a first angular position (FIG. 20) in which the injection needle movement mechanism 60 is in the first operating configuration to a second angular position (FIG. 21) in which the injection needle movement mechanism 60 is in the second operating configuration.

An abutment element 62*c* (visible in FIG. 21) extends from the outer side surface 62*a* of the support member 62 towards the pushing member 63 and a pushing element 63*c* extends from an outer side surface 63*b* of the pushing member 63 towards the support member 62.

When the injection needle movement mechanism 60 is in the first operating configuration, the pushing element 63*c* is coupled to the abutment element 62*c* and exerts a pushing action against the latter (FIG. 20), while when the injection needle movement mechanism 60 is in the second operating configuration the pushing element 63*c* is decoupled from the abutment element 62*c* (FIG. 21).

The rotation of the pushing member 63 from the first angular position to the second angular position, and therefore the shift of the injection needle movement mechanism 60 from the first operating configuration to the second operating configuration, is driven by a command member 61 arranged concentrically to the pushing member 63 and outside the latter.

The command member 61 has a substantially cylindrical shape and is driven to rotate around the axis D initially from a stop angular position (FIG. 18) in which the pushing member 63 is in the first angular position and the command member 61 is coupled to the pushing member 63 and keeps it in the first service position, to a first release angular position (FIG. 20) in which the pushing member 63 is always in the first angular position and the command member 61 is decoupled from the pushing member 63 allowing the pushing member 63 to reach the second service position.

A protruding element 63*d* extends from the outer side surface 63*b* of the pushing member 63 on the opposite side with respect to the pushing element 63*c*.

Figures 18, 19:
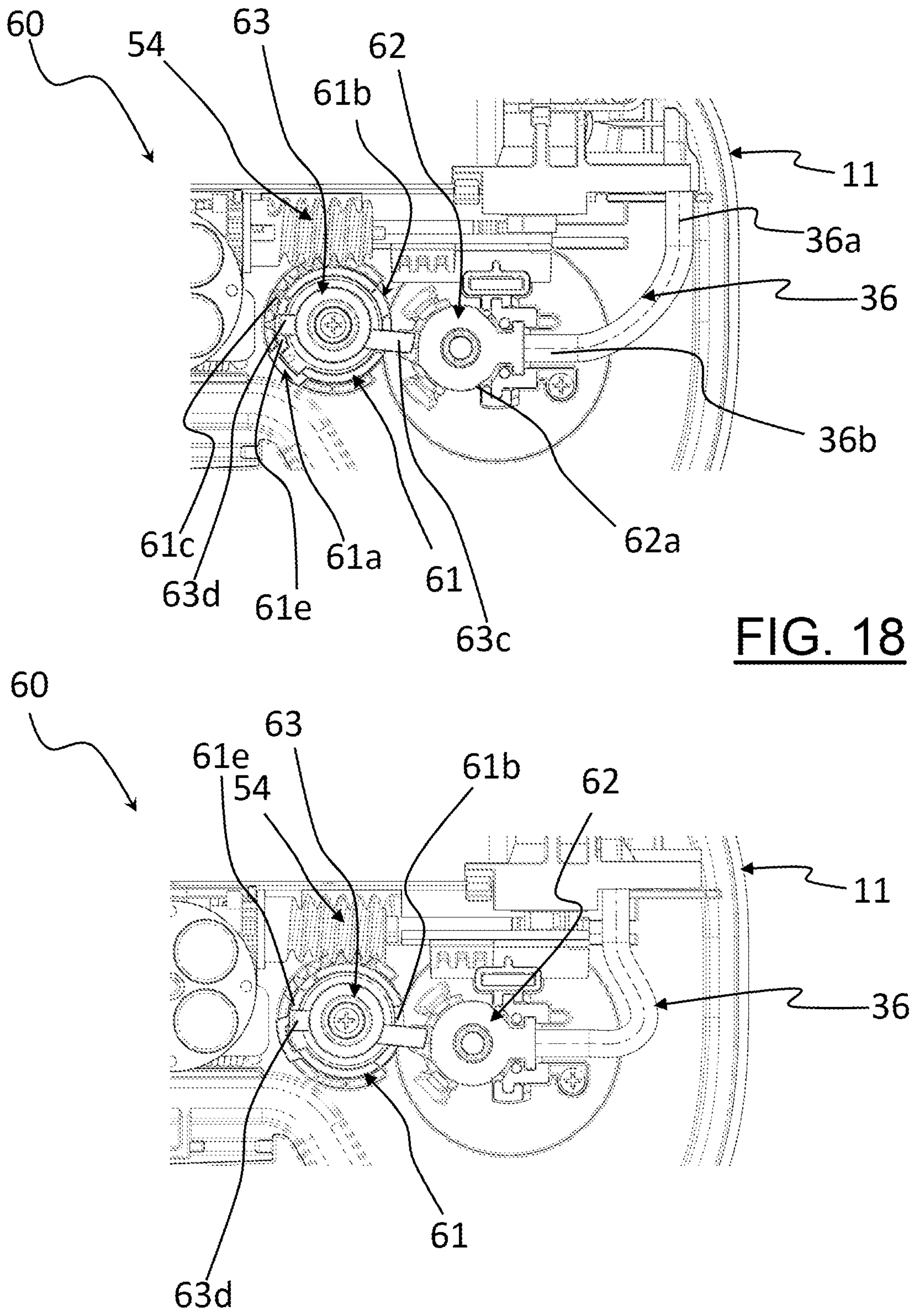
FIGS. 18-21 show an enlargement of a further portion of the module of FIG. 6 in four subsequent operating configurations of the device of FIG. 1.

The command member 61 comprises an abutment surface 61*e* which, when the command member 61 is in the stop angular position, is in abutment against the protruding element 63*d* (FIGS. 18 and 19).

The command member 61 further comprises a seat 61*a* which, when the command member 61 is in the first release angular position, houses the protruding element 63*d* (FIG. 20), and a through opening 61*b* (FIG. 18) through which the pushing element 63*c* passes to allow the pushing member 63 to couple to the support member 62.

When, following the rotation of the command member 61, the seat 61*a* is below the protruding element 63*d*, the pushing member 63 is free to move from the first service position to the second service position due to the pushing action exerted by the compression spring 65. Consequently, the support member 62 is moved from the first operating position to the second operating position due to the movement of the pushing member 63 from the first service position to the second service position and, consequently, to the thrust exerted by the pushing element 63*c* on the abutment element 62*c*, this thrust being no longer hindered by the abutment surface 61*e* of the command member 61. The injection needle 34 is thus extracted from the device 1.

The pushing element 63*c* passes through the through opening 61*b* of the command member 61 both when the pushing member 63 is in the first service position and when the pushing member 63 is in the second service position.

Subsequently, the command member 61 is driven to rotate about the axis D from the first release angular position (FIG. 20) to a second release angular position (FIG. 21) in which the pushing member 63 is in the second angular position. This rotation causes a similar rotation of the pushing member 63 due to the fact that the protruding element 63*d* is housed in the seat 61*a*.

The housing of the protruding element 63*d* in the seat 61*a* therefore allows both the shift of the pushing member 63 from the first service position to the second service position due to the thrust exerted on the pushing member 63 by the compression spring 65, with the consequent extraction of the injection needle 34 from the device 1 (FIG. 20), and the transfer of the rotary motion from the command member 61 to the pushing member 63 when it is in the second service position (FIG. 21), with the consequent release of the support member 62 by the pushing member 63 and the consequent retraction of the injection needle 34 inside the device 1 due to the thrust exerted on the support member 62 by the compression spring 64.

The command member 61 comprises a coupling portion 61*c* engaged to the endless screw 54. The coupling portion 61*c* is a toothing extended circumferentially for a predetermined angle, for example, an angle less than 180°.

As shown in FIG. 22, a suitably shaped plate 630 is arranged above the pushing member 63 and the support member 62 in order to prevent a rotation of the pushing member 63 about the axis D. This plate 630 also allows all the components of the injection needle movement mechanism 60 to be aligned and the retention of the compression springs 64 and 65 along the direction of the axis D to be ensured.

As shown in FIGS. 7, 8, 22-24, the delivery module 2 comprises also a shielding element 70 arranged around the injection needle 34 and configured to cover the tip of the injection needle 34 if the latter is in or moves into the injection position, for example because of a malfunction or failure of the injection needle movement mechanism 60, before applying the device 1 on the skin of the patient, or if the injection needle 34 accidentally remains in the injection position upon removal of the device 1 from the skin of the patient, for example because of an accidental or voluntary removal by the patient before the end of the delivery of the therapy (FIG. 23).

The shielding element 70 is movable between a first operating position (FIGS. 7 and 23) in which it protrudes from the device 1 and covers the tip of the injection needle 34 if the injection needle 34 is in the injection position (FIG. 23), and a second operating position (FIGS. 8 and 22) in which it does not protrude from the device 1.

Figure 24:
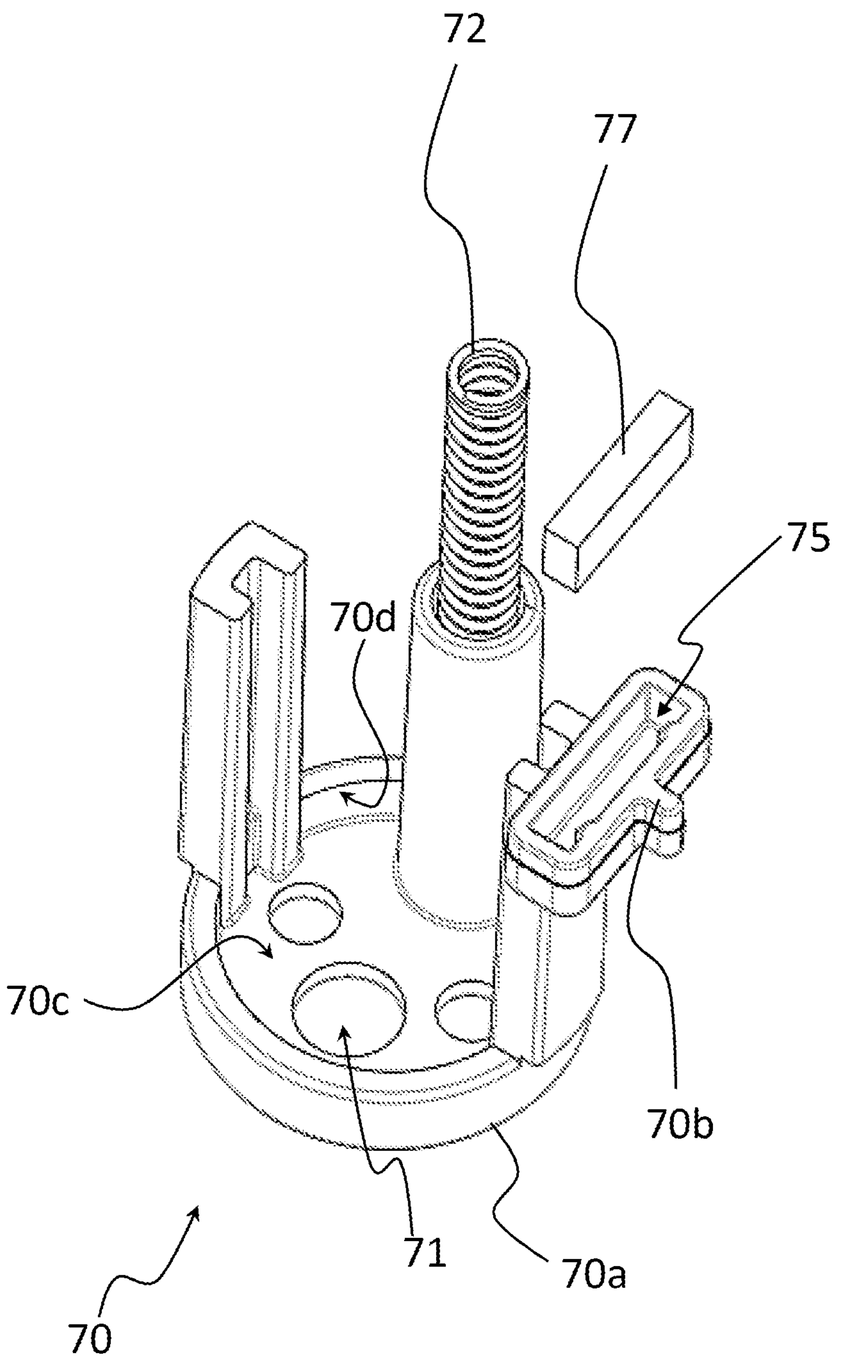
FIG. 24 is a perspective view of a component of the device of FIG. 1.

The shielding element 70 is shown in detail in FIG. 24.

Figures 7, 8:
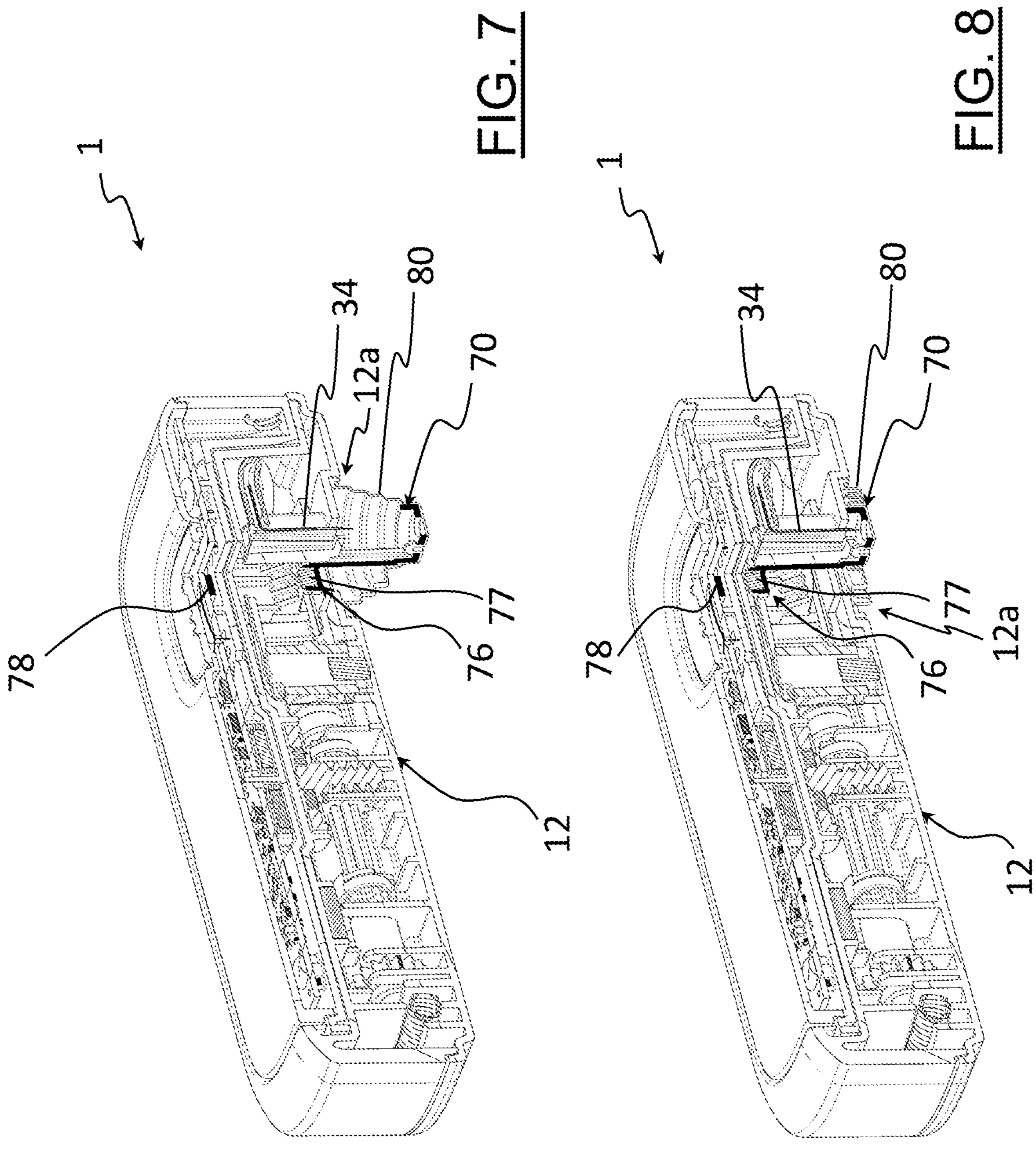
FIG. 7 is a perspective sectional view of the device of FIG. 1 before being applied on the skin of the patient.
FIG. 8 is a perspective sectional view of the device of FIG. 1 just after having been applied on the skin of the patient.

The shielding element 70 is subjected to a pushing action exerted by an elastic element 72, in particular by a compression spring. This pushing action tends to keep the shielding element 70 in the first operating position both before applying the device 1 on the skin of the patient and when the device 1 is removed from the skin of the patient (FIG. 7) and to allow the shielding element 70 to reach the second operating position when the device 1 is applied on the skin of the patient (FIGS. 8 and 22).

In particular, the elastic element 72 is arranged between the intermediate cover 15 and an inner surface 70*e* which is inside the shielding element 70 and faces toward the intermediate cover 15 (FIGS. 22 and 23).

The elastic element 72 extends along an axis E orthogonal to the plane P. The axis E is distinct from and parallel to the axes C, D and N.

With reference to FIG. 6, the delivery module 2 comprises a stop mechanism 170 configured to stop the movement of the shielding element 70.

In particular, the shielding element 70 comprises a locking element 70*b* configured to lock the shielding element 70 in the first operating position when the device 1 is removed from the skin of the patient. The locking of the shielding element 70 occurs when the locking element 70*b* interferes with a stop element 74 associated with the rack 51 at a coupling portion 55 of the rack 51 that is arranged upstream with respect to the coupling portion 52 and downstream with respect to the coupling portion 53 along the direction A, i.e. interposed between the coupling portion 53 and the coupling portion 52 (FIGS. 20 and 21).

The device 1 has an initial reversible configuration in which the shielding element 70 is free to move between the first operating position and the second operating position and vice versa before the device 1 is applied on the skin of the patient. In this configuration, the locking element 70*b*, integral with the shielding element 70, is in a distal position with respect to the stop element 74.

The device 1 has a final irreversible configuration in which the shielding element 70 is locked in the first operating position. In this configuration the locking element 70*b* is in contact with the stop element 74.

Due to the movement of the rack 51 along the direction A, the stop element 74 moves along this direction A from an initial position to a final position.

In the initial position the stop element 74 and the locking element 70*b* are not superimposed on each other and the device 1 is in the initial reversible configuration (FIGS. 18 and 19), while in the final position the stop element 74 and the locking element 70*b* are superimposed on each other and the device 1 is in the final irreversible configuration (FIGS. 20 and 21).

In some instances, the locking element 70*b* is made of a rigid material and the stop element 74 is made of a deformable material.

The switch from the reversible configuration to the irreversible configuration occurs when the stop element 74 is in the final position and the locking element 70*b* moves along a direction F (FIG. 23) orthogonal to the direction A, passing beyond the stop element 74. This movement occurs when the device 1 is removed from the skin of the patient because of the movement of the shielding element 70 from the second operating position to the first operating position due to the pushing action exerted by the elastic element 72.

The movement of the locking element 70*b* along the direction F causes at first the interference between the locking element 70*b* and the stop element 74, and subsequently the shift of the locking element 70*b* to the opposite side of the stop element 74 due to the deformation of the latter.

In particular, the stop element 74 comprises a first surface facing away from the plane P and a second surface facing toward the plane P.

The first surface allows the deformation of the stop element 74 as a consequence of the interference with the locking element 70*b* and the movement of the locking element 70*b* along the direction F from the second operating position to the first operating position.

The first surface can be inclined with respect to a plane orthogonal to the direction F, thereby facilitating the shift of the locking element 70*b* from one side to the other side of the stop element 74 as a consequence of the deformation of the latter.

The second surface instead defines an undercut which, when the device 1 is in the final irreversible configuration, prevents the movement of the locking element 70*b* from the first operating position. In some examples, the second surface is orthogonal to the direction F.

As shown in FIG. 24, the shielding element 70 has a base 70*a* provided with a through hole 71 to allow the shift of the injection needle 34 during the movement of the injection needle 34 between the rest position and the injection position when the shielding element 70 is in the second operating position.

The base 70*a* comprises a raised edge 70*d* defining in the base 70*a* a recess 70*c* that houses the tip of the injection needle 34 both when the shielding element 70 is in its second operating position and the injection needle 34 is in the rest position (FIG. 8) and when the shielding element 70 is in its first operating position and the injection needle 34 is in the injection position (FIG. 23).

Figure 33:
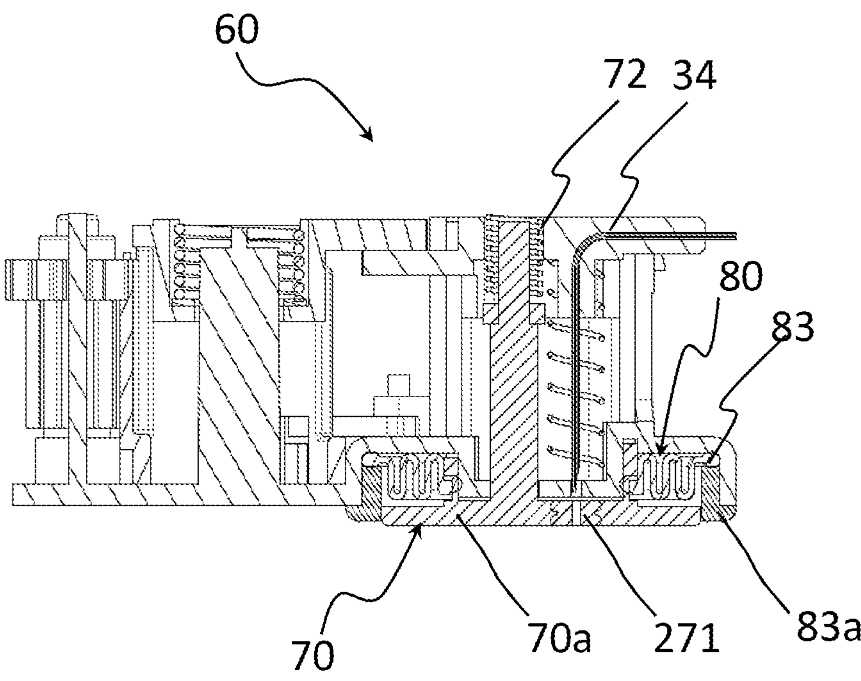
FIG. 33 is a sectional side view of the portion of FIG. 25 in the operating configuration of FIG. 26.
Figure 34:
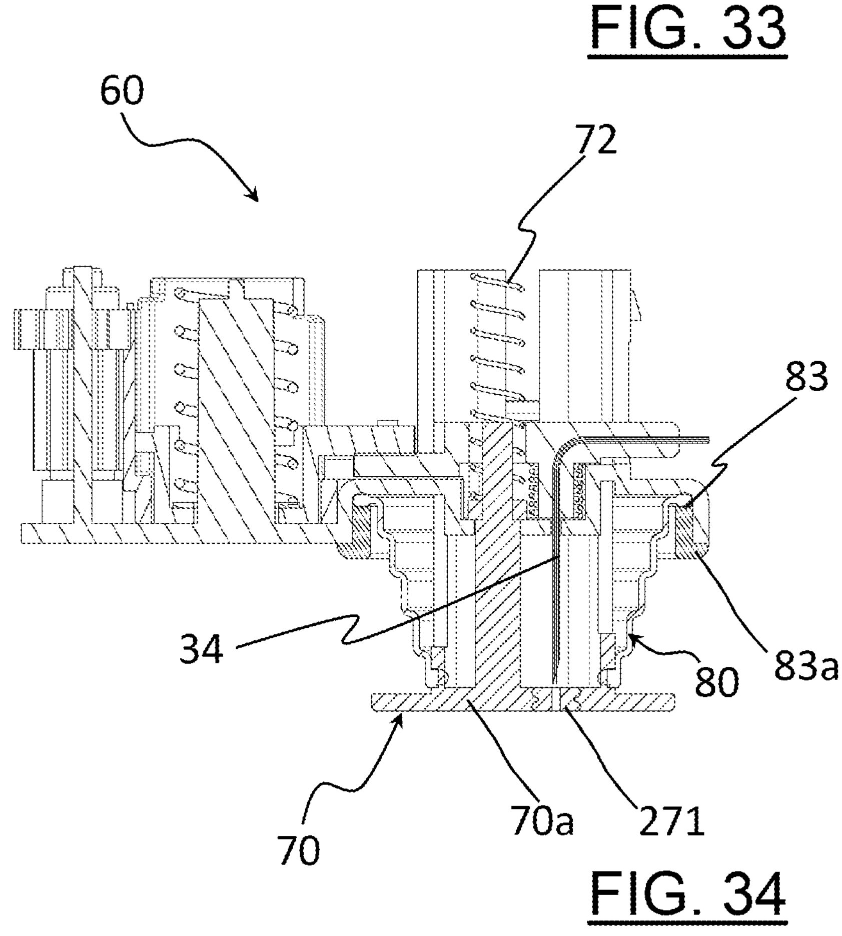
FIG. 34 is a sectional side view of the portion of FIG. 25 in the operating configuration of FIG. 32.

As shown in FIGS. 33 and 34, the through hole 71 may be closed by a pierceable septum 271.

The device 1 comprises a position sensor 76 (FIGS. 7 and 8) adapted to detect a contact of the device 1 with the skin of the patient.

The position sensor 76 comprises a magnet 77 integrally associated with the shielding element 70 and a Hall effect sensor 78 arranged in the control module 3 close to the magnet 77.

The magnet 77 is entirely housed in a seat 75 formed in the shielding element 70 (FIG. 24).

The locking element 70*b* is associated with the seat 75 close to the magnet 77.

Figure 5:
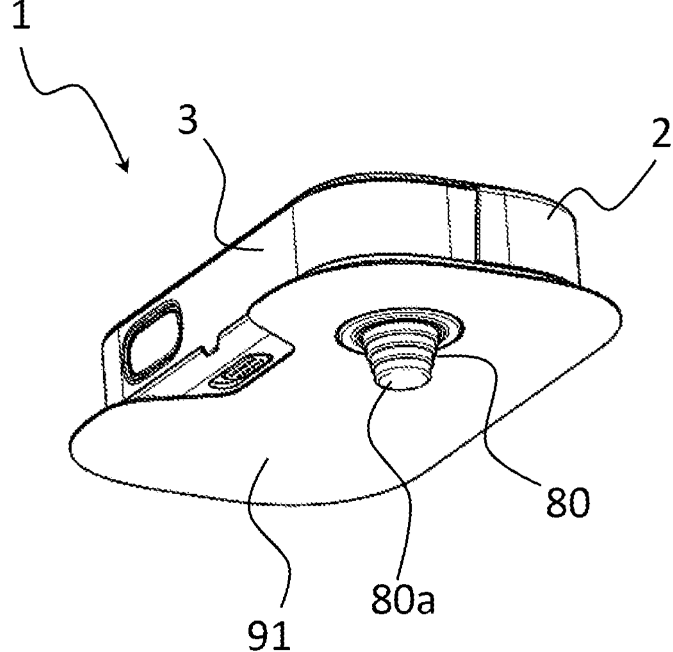
FIG. 5 is a perspective bottom view of the device of FIG. 4 after having removed a protective layer of the patch.

As shown in FIGS. 2 and 5, the device 1 further comprises a flexible sleeve 80 associated water-tightly with the application surface 12 of the delivery module 2 around the through opening 12*a*.

The flexible sleeve 80 is made of a silicone material for medical use.

The flexible sleeve 80 surrounds the shielding element 70 and comprises a base surface 80*a* having an inner surface integrally associated with the outer surface of the base 70*a* of the shielding element 70.

In the embodiment illustrated herein, the flexible sleeve 80 is defined by a bellows-type membrane having a truncated conical shape.

The flexible sleeve 80 is arranged entirely inside the delivery module 2 when the shielding element 70 is in its second operating position (FIG. 8).

The base surface 80*a* of the flexible sleeve 80 covers the through hole 71 of the shielding element 70 and is pierceable by the injection needle 34 when the injection needle 34 moves from the rest position to the injection position.

The flexible sleeve 80 comprises an annular end portion 83 fixed to the application surface 12 of the delivery module 2 through a compression ring 83*a* (FIGS. 23, 33 and 34). The latter is welded to the application surface 12 by ultrasonic welding.

The annular end portion 83 is thus interposed between the application surface 12 and the compression ring 83*a* and prevents the access of water and powders inside the device 1 through the through opening 12*a* of the application surface 12.

Figure 4:
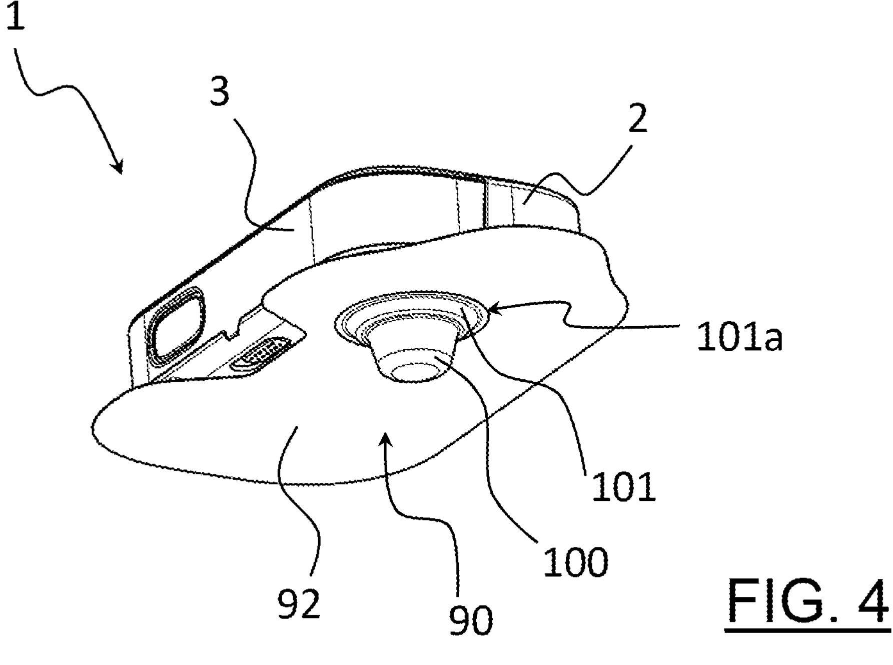
FIG. 4 is a perspective bottom view of the device of FIG. 1 provided with a patch.

As shown in FIGS. 4-5, a patch 90 is applied on the application surface 12 of the main body 11 of the delivery module 2.

The patch 90 comprises an adhesive layer 91 integrally attached to the application surface 12 and a protective layer 92 removably attached to the adhesive layer 91. Before performing the delivery of the therapy, the protective layer 92 is removed (FIG. 5) and the device 1 is attached to the skin of the patient through the adhesive layer 91.

The device 1 further comprises a cap 100 integrally attached to the protective layer 92. In particular, the cap 100 comprises a collar 101 attached to the protective layer 92 by interposition of a double-adhesive element 101*a*.

The cap 100 is made of a rigid material and is shaped so as to completely house with clearance the shielding element 70 and the flexible sleeve 80 that surrounds the shielding element 70 when the latter is in its first operating position.

In the embodiment illustrated herein, the cap 100 has a truncated conical shape.

As already mentioned, initially the shielding element 70 is in its extended configuration of FIG. 5 and the cap 100 covers the shielding element 70, as shown in FIG. 4.

Before applying the device 1 on the skin of the patient, the patient removes the protective layer 92 of the patch 90, removing simultaneously therewith also the cap 100 and thus exposing the shielding element 70 and the adhesive layer 91 of the patch 90.

The patient can then proceed to apply the device 1 on his/her skin by attaching it through the adhesive layer 91 of the patch 90. The skin of the patient counteracts the pushing action exerted by the elastic element 72 and makes the shielding element 70 retract inside the delivery module 2, bringing the magnet 77 closer to the Hall effect sensor 78 and thus allowing the control unit 7 to establish that the device 1 is in contact with the skin of the patient and to activate the delivery of the therapy.

The delivery of the therapy comprises the controlled movement of the plunger 26 inside the container 22 towards the pierceable septum 24. To this end, the delivery module 2 comprises a medicament delivery mechanism 110 (FIG. 6) which is activated, driven by the control unit 7, by the same magnetic rotor 56 that drives the motion transmission member 50 and, therefore, the rotation of the endless screw 54. As already mentioned, the latter drives both the activation of the injection needle movement mechanism 60 and the movement of the rack 51 along the direction A, which in turn drives both the opening of the fluidic path 30 and the locking of the shielding element 70 in the first operating position after the device 1 is removed from the skin of the patient.

In particular, the control unit 7 drives the magnetic rotor 56 alternately in a first rotation direction to activate the motion transmission member 50 and in a second rotation direction opposite to the first rotation direction to drive the delivery of the medicament from the container 22 upon activation of another motion transmission member 111 (FIG. 6) arranged in the main body 11 on the opposite side to the motion transmission member 50 with respect to the magnetic rotor 56 and to the endless screw 54.

FIGS. 25-34 show another embodiment of a device that differs from the device 1 described above in some details relating to the injection needle movement mechanism 60, to the shielding element 70 and to the flexible sleeve 80. The elements and/or members of this embodiment that are identical or equivalent to those described above are indicated with the same reference numeral.

In this case, the flexible sleeve 80 does not have the base surface 80*a* and the shielding element 70 has a base 70*a* having a diameter greater than that of the adjacent end portion of the flexible sleeve 80.

Also in this case, a support member 62 which supports the injection needle, a pushing member 63 and a command member 61 equivalent to those described above are provided.

Figure 25:
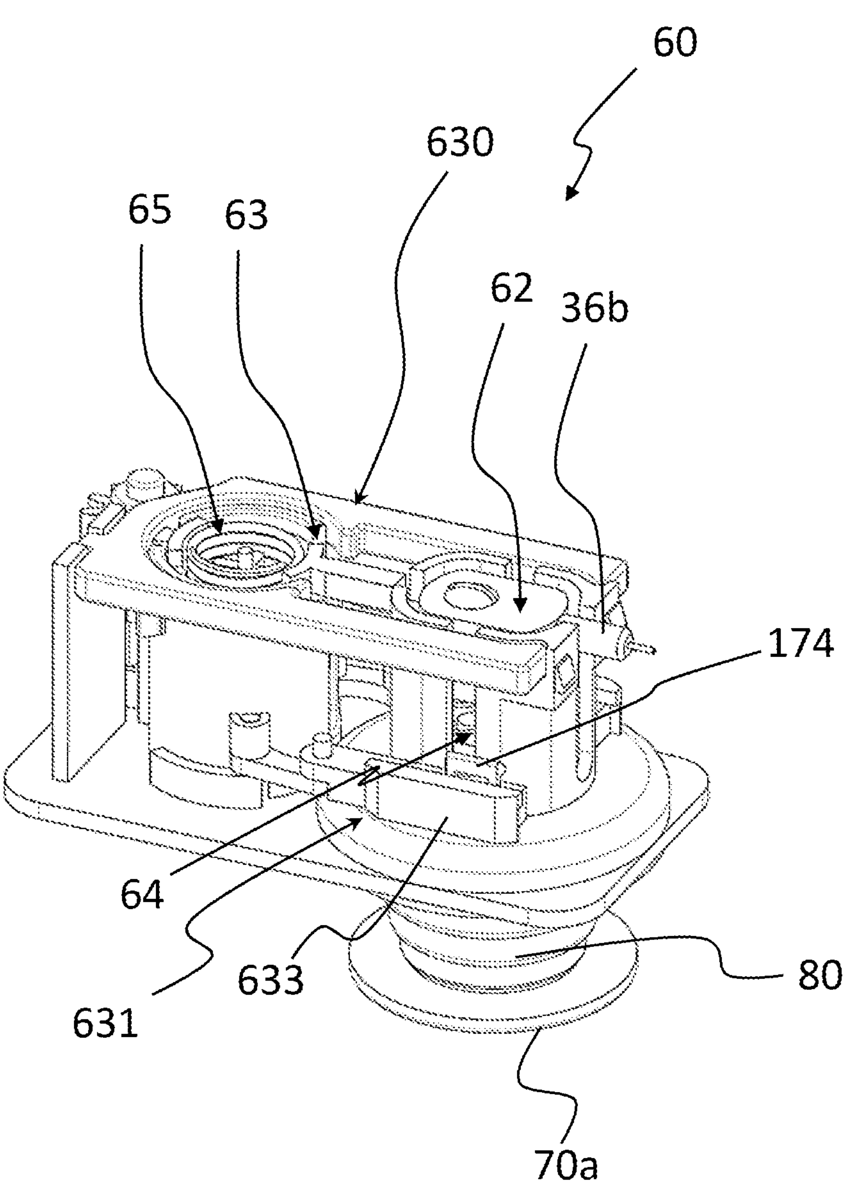
FIG. 25 is a perspective view of a portion of a third embodiment of the module of FIG. 2 when the device is not applied on the skin of the patient.

FIG. 25 shows the operating configuration in which the injection needle 34 is in the rest position and the shielding element 70 and the flexible sleeve 80 protrude from the device.

Figure 26:
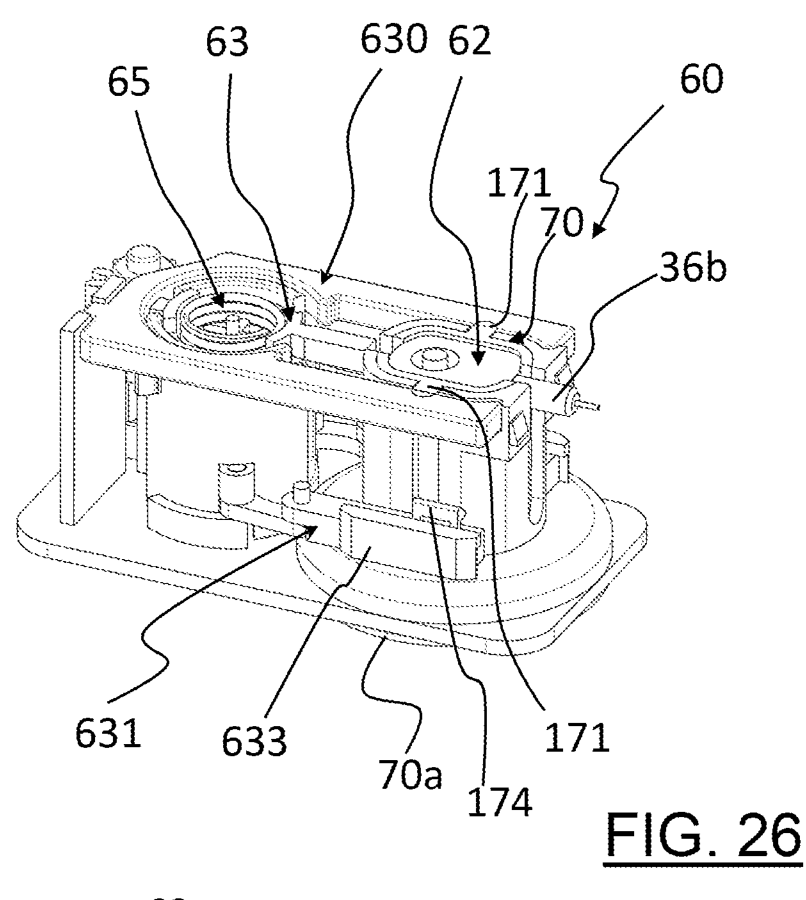
FIG. 26 is a perspective view of the portion of FIG. 25 just after having applied the device on the skin of the patient.

FIGS. 26 and 33 show the operating configuration in which the device is applied on the skin of the patient. The injection needle 34 is still in the rest position and the shielding element 70 and the flexible sleeve 80 are pushed inside the device. Only the base 70*a* of the shielding element 70 remains protruding from the device.

Figures 28, 29:
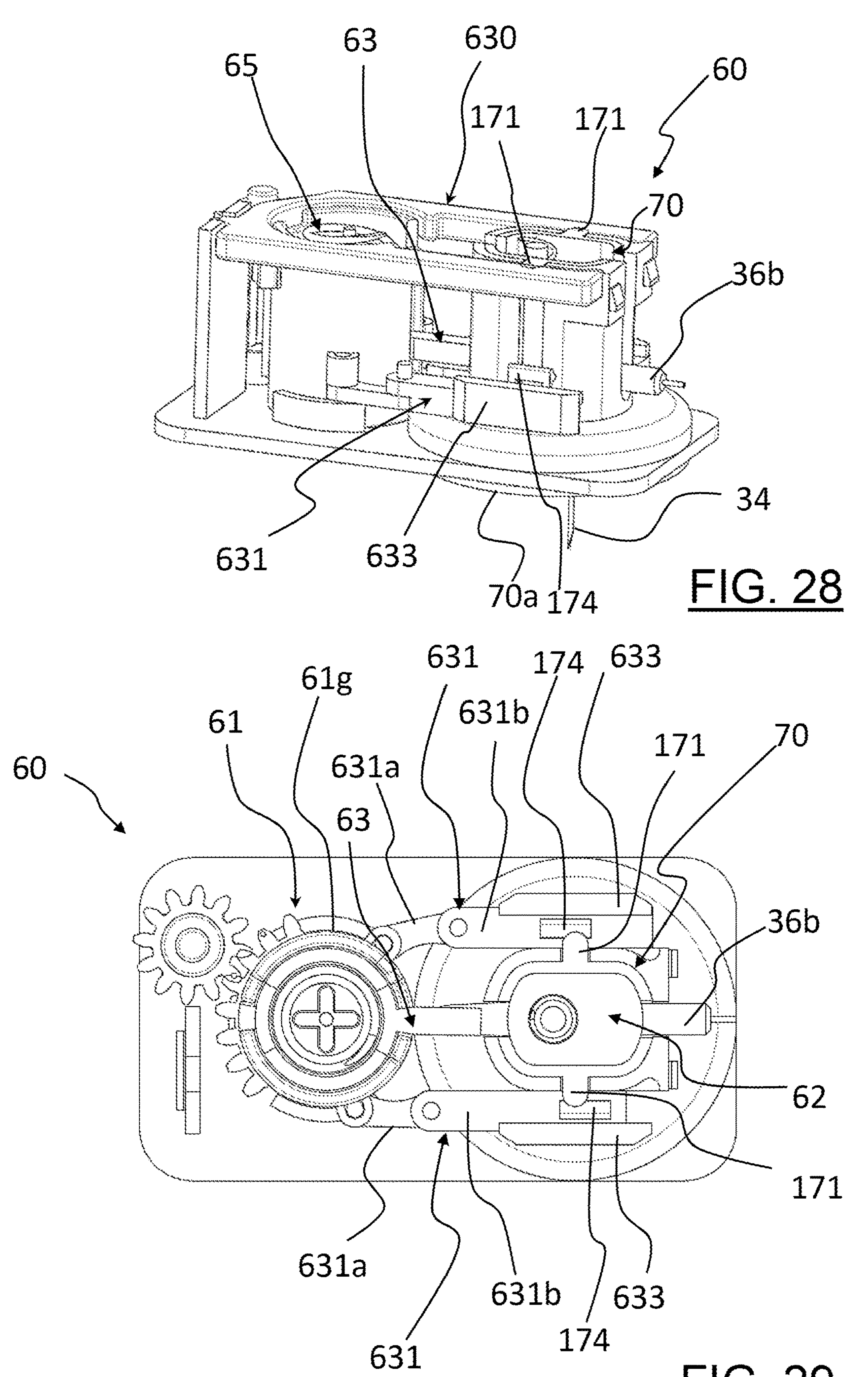
FIG. 28 is a perspective view of the portion of FIG. 25 in an operating configuration of the device subsequent to that of FIGS. 26 and 27.
FIG. 29 is a top view of the portion of FIG. 25 in the operating configuration of FIG. 28.

FIG. 28 shows the operating configuration in which the device is applied on the skin of the patient and the injection needle 34 is in the injection position to delivery the therapy. The shielding element 70 and the flexible sleeve 80 are still inside the device.

Figure 30:
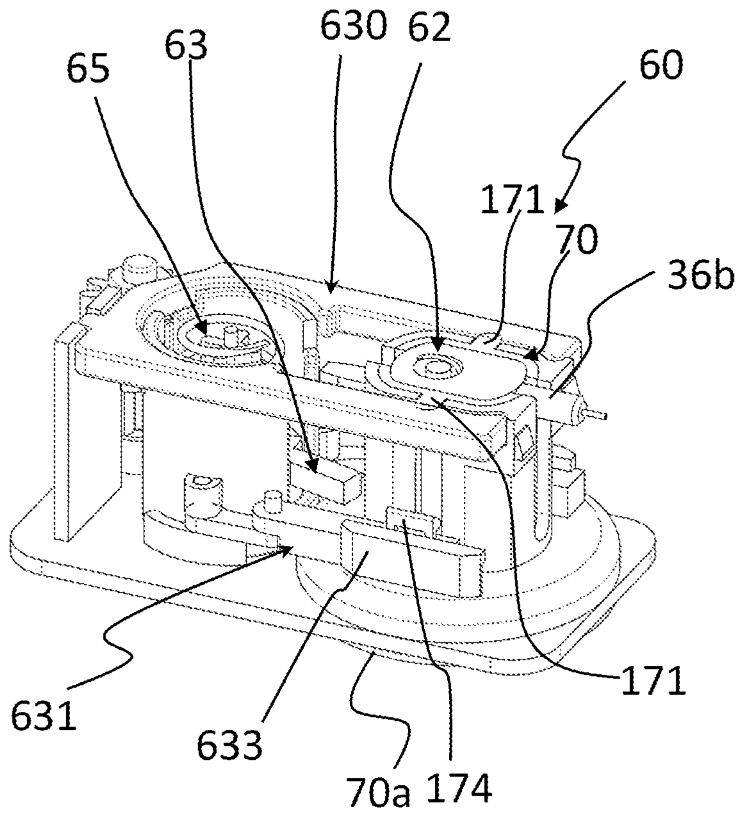
FIGS. 30-32 are perspective views of the portion of FIG. 25 in three operating configurations of the device subsequent to that of FIG. 28.

FIG. 30 shows the operating configuration in which the device is still applied on the skin of the patient but the injection needle 34 has been returned to the rest position.

Figure 31:
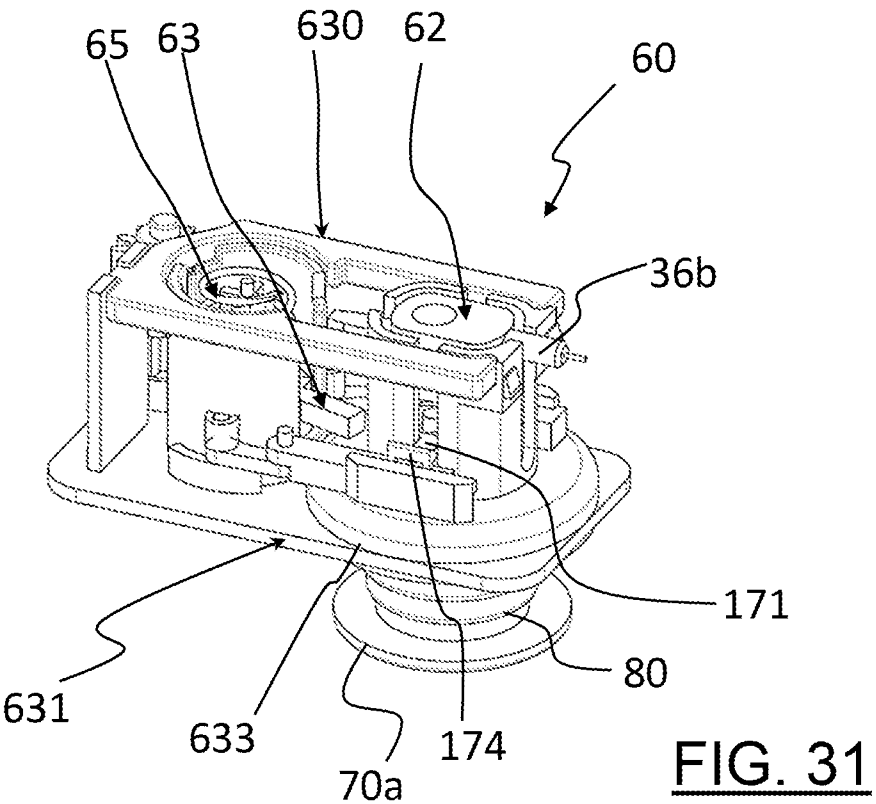

FIG. 31 shows the operating configuration in which the device is removed from the skin of the patient at the end of the delivery of the therapy. The shielding element 70 and the flexible sleeve 80 protrude from the device.

Figure 32:
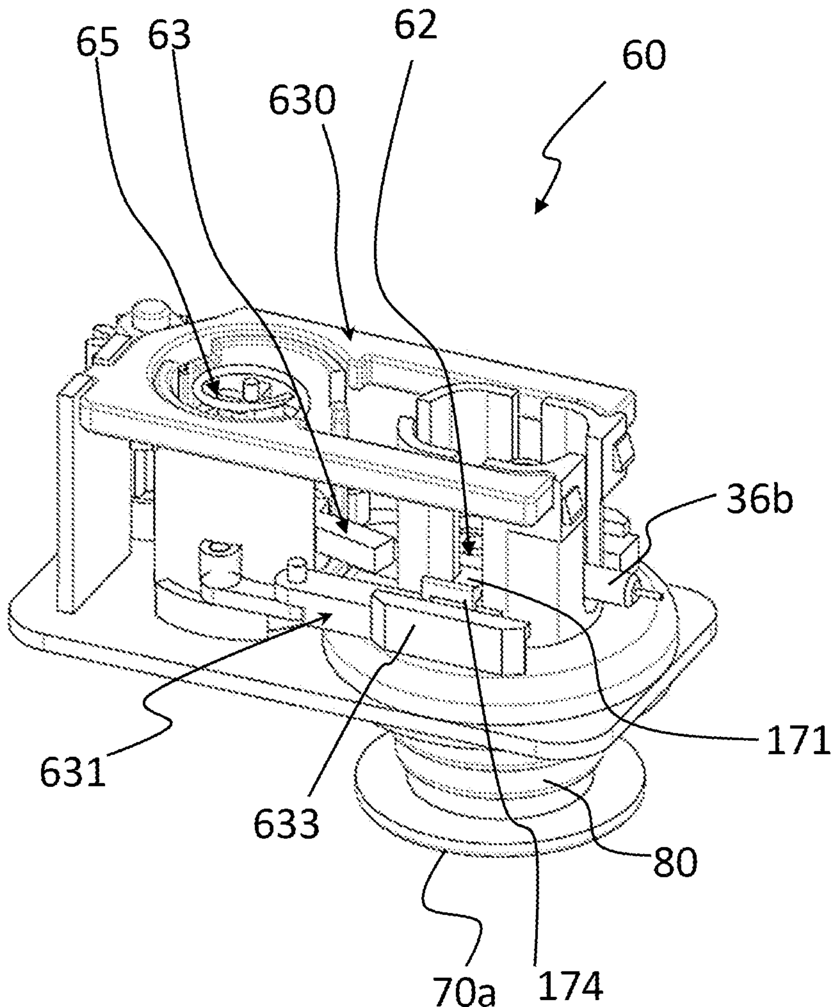

FIGS. 32 and 34 show the operating configuration in which the device is removed from the skin of the patient before the end of the delivery of the therapy and the injection needle 34 is still in the injection position. The shielding element 70 and the flexible sleeve 80 protrude from the device and the shielding element 70 is locked in position outside the device.

Figure 27:
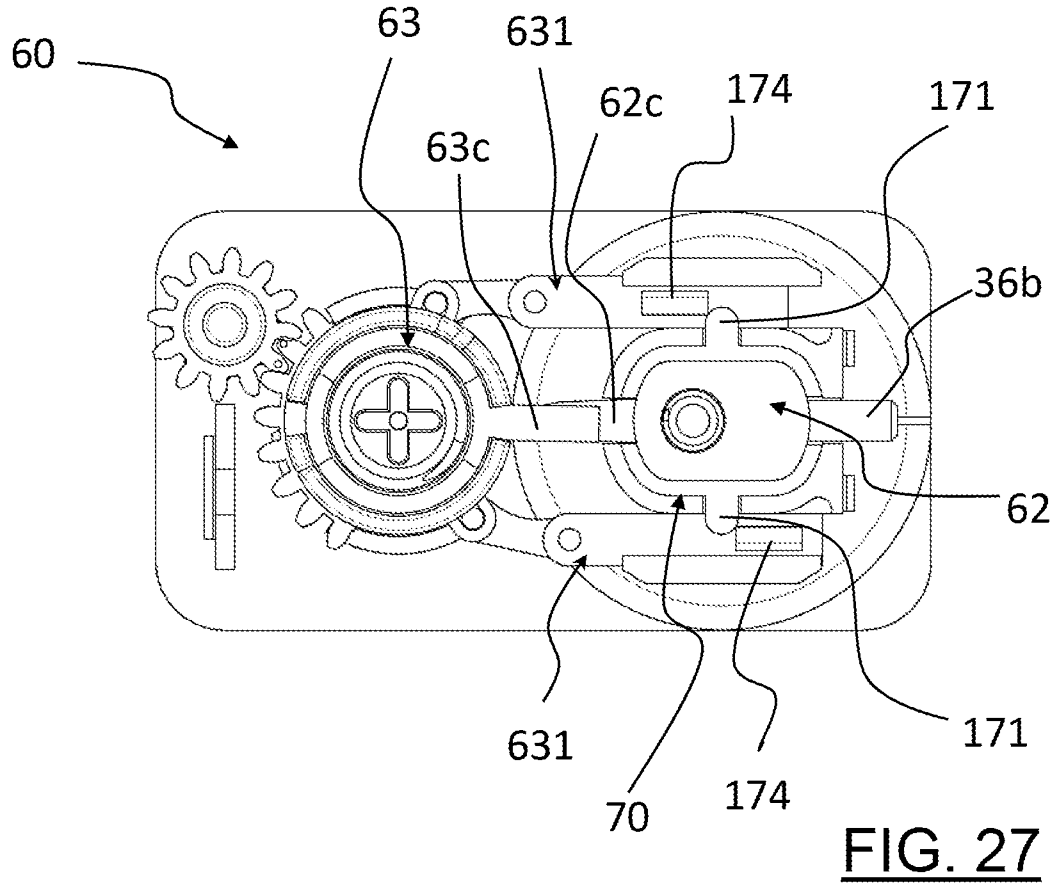
FIG. 27 is a top view of the portion of FIG. 25 in the operating configuration of FIG. 26.

In this embodiment, the command member 61 comprises two articulated arms 631 arranged on opposite sides with respect to the pushing element 63*c* (FIG. 27). As shown in FIG. 29, each articulated arm 631 comprises a first lever 631*a* hinged to the outer side surface 61*g* of the command member 61 and a second lever 631*b* hinged to the first lever 631*a*. Each second lever 631*b* is slidably coupled to a respective guide 633 and comprises a respective stop element 174 whose shape and material are similar to those of the stop element 74 described previously.

The shielding element 70 comprises two locking elements 171 arranged on diametrically opposite sides with respect to the abutment element 62*c* and configured to cooperate with the stop elements 174 (FIG. 27).

During the rotation of the command member 61 the stop elements 174 move closer to the respective locking elements 171 until each of them are at the respective locking element 171.

In the operating configuration of FIGS. 25-30, the two locking elements 171 are arranged on one side with respect to the stop elements 174, in particular close to the shaped plate 630. This is because the shielding element 70 does not protrude from the device.

When the shielding element 70 exits the device following the removal of the device from the skin of the patient, the locking elements 171 pass beyond the stop elements 174 locking the shielding element 70 in the position shown in FIG. 31. In this operating configuration the injection needle 34 has previously been returned inside the device.

If, after removal of the device from the skin of the patient, the injection needle 34 remains outside the device, as in the operating configuration of FIG. 32, the shielding element 70 and the flexible sleeve 80 protect the patient from any contacts with the injection needle 34.

Figure 35:
FIG. 35 is a time diagram relating to different operating steps implemented by the device of the present disclosure during its use.
Figure 35:
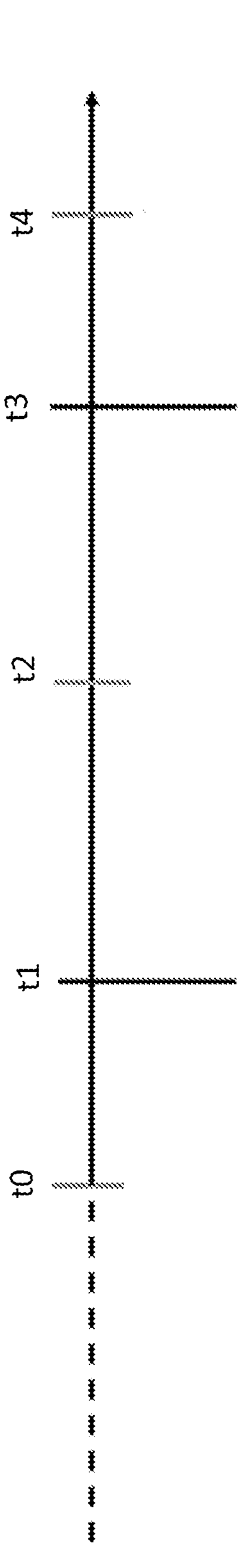

With reference also to FIG. 35, the sequence of the operating steps implemented by the device 1 during its use is described in detail hereinbelow.

During a first time interval preceding the moment to when the patient activates the device 1 by acting on the activation button 3*a*, the patient separately receives the delivery module 2 and the control module 3 and couples them. In this time interval the device 1 is in a sleep mode, i.e. the power supply battery 8 powers only some of the electronic components present in the control module 3 thanks to the provision of a hardware unit that cuts the power to all electronic components except those associated with: ignition magnet 2*a*, switch which provides power to the control unit 7, activation button 3*a* for activating the device 1 and NFC Tag 2*b*. The motor 9 is not powered.

After the mutual coupling, the delivery module 2 and the control module 3 are temporarily coupled not only mechanically but also through a magnetic coupling given by the proximity between the driving magnetic rotor 9*a* provided in the control module 3 and the magnetic rotor 56 provided in the delivery module 2. The control unit 7 switches on thanks to a change in magnetic field generated by the mutual approach between the ignition magnet 2*a* and the switch which provides power to the control unit 7 are closer. This mutual approach triggers the abovementioned switch, which switches the control unit 7 on.

Once switched on, the control unit 7 performs a self-diagnosis.

In addition, after switching on, the control unit 7 queries the NFC Tag 2*b* by reading the information stored therein. In particular, the control unit 7 performs any one or all of the following actions: check if the delivery module 2 has already been used, check if the delivery module 2 is configured to deliver a correct dosage of the medicament, establish the method of delivery of the medicament, establish the speed of delivery of the medicament.

After switching on, the control unit 7 also reads the signal of the position sensor 76 to establish if the device 1 is in contact with the skin of the patient.

In particular, the patient removes the protective layer 92 of the patch 90, removing simultaneously therewith also the cap 100, and applies the device 1 on his/her skin.

In the abovementioned time interval preceding the moment to and before applying device 1 on the skin of the patient:

- the fluidic path 30 is closed, i.e., the piercing needle 32 is in a distal position with respect to the pierceable septum 24 and the elastic element 46 is compressed;
- the shielding element 70 is in its first operating position, i.e., it protrudes from the device 1 and the elastic element 72 is extended;
- due to the distance between magnet 77 and Hall effect sensor 78, the position sensor 76 signals to the control unit 7 that the device 1 has not yet been applied on the body of the patient;
- the injection needle movement mechanism 60 is deactivated, i.e., the injection needle 34 is in the rest position, inside the device 1;
- the flexible sleeve 80 is extended.

In the abovementioned time interval preceding the moment to, after applying the device 1 on the skin of the patient:

- the fluidic path 30 remains closed;
- the shielding element 70 is in its second operating position, i.e., it is arranged inside the device 1 and the elastic element 72 is compressed;
- due to the mutual approach between magnet 77 and Hall effect sensor 78, the position sensor 76 signals to the control unit 7 that the device has been applied on the body of the patient and the control unit 7 can be activated for the delivery of the therapy;
- the injection needle movement mechanism 60 remains deactivated;
- the flexible sleeve 80 is folded inside the device 1.

If the control unit 7 does not detect the signal of the position sensor 76 within a predetermined time, the control unit 7 switches off and the device 1 returns to the sleep mode.

At this point (i.e. at time t0) the device 1 is put into operation by the patient by pressing the activation button 3*a*. The motor 9 is activated and the control unit 7 commands a series of operations that do not require any action on the part of the patient.

In a time interval t1 subsequent to the time to and lasting for example 10-15 seconds, the magnetic rotor 56 is set in rotation in the first rotation direction by the motor 9 and activates the motion transmission member 50, which in turn simultaneously activates the fluidic path opening system 40 (the piercing needle 32 pierces the pierceable septum 24 and the elastic element 46 extends) and the injection needle movement mechanism 60 without however moving the injection needle 34, which remains in the rest position.

In particular, the rotation of the endless screw 54 causes the movement of the rack 51 along the direction A and the consequent rotation of the driving member 48 and opening of the fluidic path 30. This rotation also causes the rotation of the command member 61 which moves from the stop angular position of FIG. 18 to another stop angular position, shown in FIG. 19. This rotation does not cause any rotation of the pushing member 63, which remains in the first service position due to the fact that the protruding element 63*d* remains in abutment against the abutment surface 61*e*.

In a time interval t2 subsequent to the time interval t1 and lasting for example 8-12 seconds, the magnetic rotor 56 is set in rotation in the second rotation direction by the motor 9 and activates the motion transmission member 111, causing the movement of the plunger 26 inside the container 22. Such movement causes the exit of the medicament through the piercing needle 32 but not also the delivery of the medicament through the injection needle 34. The thrust exerted by the plunger 26 on the medicament causes the air contained in the fluidic path 30 to exit (priming phase).

In a time interval t3 subsequent to the time interval t3 and lasting for example 8-12 seconds, the magnetic rotor 56 is set again in rotation in the first rotation direction by the motor 9 and activates the motion transmission member 50 again, causing the reactivation of the injection needle movement mechanism 60.

In particular, the rotation of the endless screw 54 causes a further rotation of the command member 61 which moves from the stop angular position of FIG. 19 to the first release angular position of FIG. 20. This rotation causes the movement of the pushing member 63 from the first service position to the second service position and, consequently, the movement of the support member 62 (and therefore of the injection needle 34) from the first operating position (injection needle 34 in the rest position) to the second operating position (injection needle 34 in the injection position). The injection needle 34 thus penetrates the skin of the patient.

In a time interval t4 subsequent to the time interval t3 and lasting for example 2-5 seconds, the magnetic rotor 56 is set again in rotation in the second rotation direction by the motor 9 and activates again the motion transmission member 111, causing the movement of the plunger 26 inside the container 22 which this time causes the delivery of the medicament into the body of the patient through the injection needle 34. In this phase it can still happen that a very limited amount of air, remained inside the fluidic path 30 after the priming phase, is expelled from the fluidic path.

Subsequent to the time interval t4, the motor 9 drives the magnetic rotor 56 once again in the first rotation direction reactivating the motion transmission member 50 and causing the reactivation of the injection needle movement mechanism 60.

In particular, the rotation of the endless screw 54 causes a further rotation of the command member 61 which moves from the first release angular position of FIG. 20 to the second release angular position of FIG. 21. This rotation causes a similar rotation of the pushing member 63 due to the fact that the protruding element 63*d* is housed in the seat 61*a* and, consequently, the decoupling between the pushing element 63*c* and the abutment element 62*c*. At this point, the force exerted by the compression spring 64 on the support member 62 moves it from the second operating position to the first operating position, leaving the pushing member 63 in the second service position. The injection needle 34 thus returns to the rest position, i.e. inside the device 1.

The control unit 7 emits an end of therapy signal n seconds after having driven the movement of the command member 61 from the first release angular position of FIG. 20 to the second release angular position of FIG. 21, so as to be sure that the patient can remove the device from his/her skin when the injection needle 34 has returned to the rest position, i.e. it is inside the device 1.

The emission of the end of therapy signal by the control unit is communicated to the patient through visual and/or acoustic signals.

The patient can then remove the device 1 from his/her skin.

The removal of the device 1 from the body of the patient causes the movement of the shielding element 70 (and consequently of the flexible sleeve 80) from the second operating position (shielding element 70 inside the device 1 and flexible sleeve 80 folded inside the device 1) to the first operating position (shielding element 70 outside the device 1 and flexible sleeve 80 extended outside the device 1) due to the thrust exerted on the shielding element 70 by the elastic element 72 and, consequently, the locking of the shielding element 70 in the first operating position due to the movement of the locking element(s) 70*b*, 171 from one side to the other side of the stop element(s) 74, 174 and of the abutment between the locking element(s) 70*b*, 171 and the second surface of the stop element 74, 174 facing toward the plane P.

What is claimed is:

1. A device for subcutaneous delivery of a medicament, comprising:

an injection needle configured to receive the medicament from a cartridge through a flexible tube and to inject the medicament to a patient; and an injection needle movement mechanism configured to move the injection needle between a rest position in which the injection needle is entirely arranged within the device and an injection position in which the injection needle protrudes at least partially from the device;

wherein the injection needle movement mechanism comprises:

a pushing member movable from a first service position in which the injection needle is in the rest position to a second service position in which the injection needle is in the injection position;

a first compression spring configured to exert a force on the pushing member to move the pushing member from the first service position to the second service position, the first compression spring extending along a first axis;

a support member on which the injection needle is mounted, the support member being movable between a first operating position in which the injection needle is in the rest position and a second operating position in which the injection needle is in the injection position, the support member comprising, on an outer side surface thereof, a coupling portion coupled to the flexible tube; and a second compression spring configured to exert a force on the support member to move the support member from the second operating position to the first operating position, the second compression spring extending along a second axis that is distinct from the first axis;

wherein the injection needle movement mechanism has a first operating configuration in which the pushing member is coupled to the support member and the force exerted by the first compression spring on the pushing member moves the pushing member from the first service position to the second service position and moves the support member from the first operating position to the second operating position loading the second compression spring and a second operating configuration in which the pushing member is decoupled from the support member and the force exerted by the second compression spring on the support member moves the support member from the second operating position to the first operating position; and wherein the pushing member is movable around the first axis from a first angular position in which the injection needle movement mechanism is in the first operating configuration to a second angular position in which the injection needle movement mechanism is in the second operating configuration.

2. The device of claim 1, wherein, when the injection needle movement mechanism is in the second operating configuration, the pushing member is in the second service position.

3. The device of claim 2, wherein the first compression spring has a first elastic constant greater than a second elastic constant of the second compression spring.

4. The device of claim 3, wherein the pushing member is movable around the first axis from a first angular position in which the injection needle movement mechanism is in the first operating configuration to a second angular position in which the injection needle movement mechanism is in the second operating configuration.

5. The device of claim 1, wherein the first compression spring has a first elastic constant greater than a second elastic constant of the second compression spring.

6. The device of claim 1, wherein the support member comprises an abutment element and the pushing member comprises a pushing element which, when the injection needle movement mechanism is in the first operating configuration, exerts a pushing action against the abutment element.

7. The device of claim 6, wherein the abutment element protrudes from the outer side surface of the support member towards the pushing member, and the pushing element protrudes from an outer side surface of the pushing member towards the support member.

8. The device of claim 6, wherein the injection needle movement mechanism comprises a command member configured to move the pushing member from the first angular position to the second angular position.

9. The device of claim 1, wherein the injection needle movement mechanism comprises a command member configured to move the pushing member from the first angular position to the second angular position.

10. The device of claim 9, wherein the command member is movable around the first axis from a stop angular position in which the pushing member is in the first angular position and the command member is coupled to the pushing member and retains the pushing member in the first service position, to a first release angular position in which the pushing member is in the first angular position and the command member is decoupled from the pushing member allowing the pushing member to reach the second service position.

11. The device of claim 10, wherein the pushing member comprises a protruding element, and the command member comprises:

an abutment surface configured to abut against the protruding element when the command member is in the stop angular position; and a seat configured to house the protruding element when the command member is in the first release angular position.

12. The device of claim 11, wherein the command member is movable around the first axis from the first release angular position to a second release angular position in which the pushing member is in the second angular position.

13. The device of claim 12, wherein, when the command member is in the second release angular position, the protruding element is housed in the seat.

14. The device of claim 10, wherein the command member is movable around the first axis from the first release angular position to a second release angular position in which the pushing member is in the second angular position.

15. The device of claim 7, comprising a motion transmission member configured to activate a shift of the injection needle movement mechanism from the first operating configuration to the second operating configuration.

16. The device of claim 15, wherein the command member comprises a coupling portion coupled to the motion transmission member.

17. The device of claim 16, wherein the motion transmission member comprises a rack and an endless screw engaged to the rack at the coupling portion, and the command member comprises a toothing engaged to the endless screw.

18. The device of claim 15, wherein the motion transmission member comprises a rack and an endless screw engaged to the rack at a coupling portion of the rack, and the command member comprises a toothing engaged to the endless screw.

19. The device of claim 1, comprising a motion transmission member configured to activate the shift of the injection needle movement mechanism from the first operating configuration to the second operating configuration.

* * * * *